(12) United States Patent
Creighton

(10) Patent No.: US 12,070,560 B2
(45) Date of Patent: Aug. 27, 2024

(54) MAGNETICALLY CONTROLLED LINKAGE BASED DEVICES

(71) Applicant: UNandUP, LLC., Saint Louis, MO (US)

(72) Inventor: Francis M. Creighton, St. Louis, MO (US)

(73) Assignee: UNandUP, LLC, St. Louis, MO (US)

(*) Notice: Subject to any disclaimer, the term of this patent is extended or adjusted under 35 U.S.C. 154(b) by 451 days.

(21) Appl. No.: 16/905,869

(22) Filed: Jun. 18, 2020

(65) Prior Publication Data

US 2020/0330727 A1    Oct. 22, 2020

Related U.S. Application Data

(63) Continuation-in-part of application No. 16/851,699, filed on Apr. 17, 2020.
(Continued)

(51) Int. Cl.
*A61M 25/00* (2006.01)
*A61B 18/00* (2006.01)
*A61M 25/01* (2006.01)

(52) U.S. Cl.
CPC ......... *A61M 25/0127* (2013.01); *A61B 18/00* (2013.01); *A61M 25/0147* (2013.01); *A61M 25/0158* (2013.01); *A61B 2018/00577* (2013.01); *A61M 2025/0161* (2013.01); *A61M 2210/125* (2013.01)

(58) Field of Classification Search
CPC .......... A61M 25/0127; A61M 25/0158; A61M 2025/0166
See application file for complete search history.

(56) References Cited

U.S. PATENT DOCUMENTS

| | | | |
|---|---|---|---|
| 4,005,699 A | | 2/1977 | Bucalo |
| 5,916,147 A | * | 6/1999 | Boury ............... A61M 25/0147 600/149 |

(Continued)

FOREIGN PATENT DOCUMENTS

| | | | |
|---|---|---|---|
| EP | 3053625 A2 | * 8/2016 | ......... A61B 1/00158 |
| JP | 2013000222 A | 1/2013 | |
| WO | 0193939 A1 | 12/2001 | |

*Primary Examiner* — William R Carpenter
(74) *Attorney, Agent, or Firm* — Polsinelli PC

(57) ABSTRACT

A magnetically controllable linkage based medical device for interventional medical procedures includes a magnetic tip subassembly including magnet elements thereon; a plurality of linkage body elements connected in sequence, a distal linkage body element coupled to the magnetic tip subassembly, wherein each linkage body element is configured for deflection in at least one deflection direction; a linkage base element coupled to a proximal linkage body element; a support body connected to the linkage base element; at least one pair of control wires passing to the magnetic tip subassembly; wherein the device is configured such that an externally-generated magnetic field deflects the magnetically-controlled linkage-based device in at least one deflection direction, and wherein selectively tensioning the control wires can hold the magnetically-controlled linkage-based device in a desired orientation. The device is configured such that the externally-generated magnetic field which deflects the magnetically-controlled linkage-based device is less than 40 millitesla.

20 Claims, 17 Drawing Sheets

Related U.S. Application Data

(60) Provisional application No. 62/868,972, filed on Jun. 30, 2019, provisional application No. 62/835,695, filed on Apr. 18, 2019.

(56) References Cited

U.S. PATENT DOCUMENTS

| | | | |
|---|---|---|---|
| 5,931,818 | A | 8/1999 | Werp et al. |
| 6,292,678 | B1 | 9/2001 | Hall et al. |
| 6,375,606 | B1 | 4/2002 | Garibaldi et al. |
| 6,817,364 | B2 | 11/2004 | Garibaldi et al. |
| 6,926,669 | B1 * | 8/2005 | Stewart ............ A61M 25/0147 601/3 |
| 7,066,924 | B1 | 6/2006 | Garibaldi et al. |
| 7,603,905 | B2 | 10/2009 | Creighton, IV |
| 7,757,694 | B2 | 7/2010 | Ritter et al. |
| 7,771,415 | B2 | 8/2010 | Ritter et al. |
| 7,974,678 | B2 | 7/2011 | Maschke |
| 8,092,450 | B2 | 1/2012 | Davies et al. |
| 8,419,681 | B2 | 4/2013 | Sell |
| 2002/0072758 | A1 | 6/2002 | Reo et al. |
| 2003/0144657 | A1 * | 7/2003 | Bowe ................ A61M 25/0133 606/41 |
| 2005/0203382 | A1 * | 9/2005 | Govari ............. A61M 25/0147 600/424 |
| 2006/0079812 | A1 | 4/2006 | Viswanathan |
| 2006/0247522 | A1 * | 11/2006 | McGee ............. A61M 25/0144 600/434 |
| 2007/0016131 | A1 | 1/2007 | Munger et al. |
| 2008/0312673 | A1 * | 12/2008 | Viswanathan ......... A61B 90/36 606/159 |
| 2012/0238806 | A1 * | 9/2012 | Mangiardi ............ A61F 2/958 600/106 |

* cited by examiner

MAGNETICALLY CONTROLLED LINKAGE BASED DEVICES

RELATED APPLICATIONS

This application is a continuation in part of application Ser. No. 16/851,699, filed Apr. 17, 2020 and titled "Magnetically Controlled Medical Devices for Interventional Medical Procedures and Methods of Making and Controlling the Same" which is incorporated herein by reference.

This application claims priority to U.S. Patent Application Ser. No. 62/835,695, filed Apr. 18, 2019 titled "Magnetically Controlled Linkage Based Devices" which is incorporated herein by reference.

This application claims priority to U.S. Patent Application Ser. No. 62/868,972, filed Jun. 30, 2019 titled "Novel Magnetically-Controlled Programmable Magnetic Devices" which is incorporated herein by reference.

Application Ser. No. 16/851,699, claims priority to U.S. Patent Application Ser. No. 62/835,695, filed Apr. 18, 2019 titled "Magnetically Controlled Linkage Based Devices" which is incorporated herein by reference.

Application Ser. No. 16/851,699, claims priority to U.S. Patent Application Serial Number, filed Jun. 30, 2019 titled "Novel Magnetically-Controlled Programmable Magnetic Devices" which is incorporated herein by reference.

BACKGROUND INFORMATION

1. Field of the Invention

The present invention relates to magnetically controllable linkage based medical devices for interventional medical procedures, and methods of making and controlling the same.

2. Background Information

The use of magnetic fields in medicine is not new. In 1873, Dr. Julius Hirschberg is often credited with being the first to use an electromagnet to remove iron filings from the eye. From that time onward, magnetism in medicine quickly expanded, including uses of iron compounds to deliver hyperthermia for tumors in 1957, thrombosis inducement within aneurysm sacks in 1965, embolization of tumors in 1973, and to enhanced imaging for MR procedures in 1982, to name a few milestones. The present invention is directed to the field of controlling medical devices in interventional medical procedures, which conventionally are manually controlled, or now sometimes robotically controlled.

Within the meaning of the present invention the phrase "interventional medical procedure" refers to medical procedures conducted within a body lumen, a body cavity and/or a body chamber. Further, medical devices for interventional medical procedures are devices constructed for performing medical procedures and treatments within a body lumen, a body cavity and/or a body chamber.

Manually-controllable medical devices for interventional medical procedures, e.g., guidewires, coils, lumens, microcatheters, catheters, sheaths, can be difficult to navigate within the designated body lumen, a body cavity and/or a body chamber. As a result, their use can lead to long procedure times, expose operators and patients to increased ionizing radiation, and contribute to poor clinical patient outcomes. Manually-controllable catheters and other navigable sheaths may be considered more complex in their design than guidewires and coils. Thus, methods to navigate these devices can be thus more complicated. As a result, again, their use can contribute to poor clinical outcomes, can lead to long procedure times, and can expose operators and patients to hazards.

Manually-deflectable catheters rely on complex tension-wire designs that are operated from nearly a meter away, thus errors can accumulate in the transmission of forces and torques. Even using catheters which can measure forces at the tip, catheter navigation and tissue contact remain suboptimal and can lead to ineffective treatment or injury. As a result, catheter navigation and tissue contact can be challenging. Catheter navigation for therapeutic purposes generally requires a skilled operator Robotic platforms have attempted to address common manual catheter navigation deficiencies. For example, robotic platforms have been developed to overcome manual ablation catheters deficiencies. Standard robotic systems interface with manual catheters and place the operator outside the imaging field, where imaging includes but is not limited to x-ray, computer tomography, camera-based, ultrasound, and magnetic resonance imaging. Studies show these robotic systems do not improve navigational precision, catheter tip control is relatively unimproved, they are associated with more adverse events, and have a high learning curve. In addition, these systems can be expensive.

In comparison, magnet-based robotic systems have improved upon standard robotic limitations by using magnetic fields to deflect the catheters, resulting in improved catheter navigation and better tissue contact. Having performed more than 100,000 magnet-based procedures, the platform of Stereotaxis Inc. is the most-successful magnetic robotic platform for navigating magnet-tipped catheters as of 2018. Because the Stereotaxis platform must use a relatively high magnetic field (about 100 milli-tesla) to properly deflect their magnet-tipped catheters, several shortcomings result. First, the Stereotaxis platform is very expensive given that the technology consists of two approximately 500-kilogram permanent magnets housed in two approximately 1500-kilogram positioners. Second, the high magnet field employed requires the Stereotaxis platform to be used in a magnetically-shielded suite with the control room separately located. Third, the large magnet field employed requires a custom magnetically-compatible x-ray system to be used. Fourth, only Stereotaxis' catheters are compatible with the Stereotaxis system. Fifth, because the Stereotaxis platform is large, setup and procedures times can be long. Sixth, Stereotaxis' catheters are unable to generate sufficient tissue contact forces to perform successful therapies. Seventh, the Stereotaxis platform possesses a complex interface. And eighth, sheaths must be used to overcome the inability to fully orient the Stereotaxis' catheter.

Generally speaking, all existing catheters (manual and robotic) possess a common limitation: the catheter's tip angle is fixed over the deflection's range. As a result, the catheter's tip angle is unable to be oriented in a preferential way. Instead, there is one and only tip orientation for each catheter deflection angle. For some deflection angles, the tip is aligned with the tissue so that therapy is applied in the most effective manner and orientation. However, for all other catheter deflection angles, the tip angle must also change, thereby negatively impacting the ability to deliver therapy. Furthermore, deflection of the catheter results in forces only along the deflection curve and not inward or outward. To generate forces against tissue, the catheter tip's side must be pressed against the tissue. As a result, intermittent contact, catheter drift, or a poor catheter tip-angle can prevent the delivery of effective therapy. For excessive forces, tissue perforations can occur.

The advantage of the Stereotaxis platform is the ability to magnetically generate forces and torques on the catheter's tip, which avoids sources of variability that accumulate along the catheter's length. Magnetically-navigated catheters are like manual catheters in that electrical and irrigation conduits are contained within. However, the deflection wires necessary for manual catheters are removed, and magnets are added along the end and near the catheter's tip. Unlike manual catheters, which only deflect in a plane, magnetic catheters can bend in any direction. To ensure sustained tissue contact, the catheter is deflected so that the spring-like restoring force pushes outward against the tissue. This strategy is the driver of the Stereotaxis platform's need for a strong magnetic field (about 100 milli-tesla, which, for reference, is about 200-times greater than the earth's magnetic field). As a result, much of the magnetic energy is spent fighting the catheter's restoring force, tissue contact forces tend to be weak and cannot be reliably directed in all directions, and additional sheaths are needed to ensure that inherent magnetic instabilities do not cause the catheter to flip 180 degrees.

To explain these limitations, it is instructive to consider a simplified model for the catheter's restoring torque: $\tau_r = \lambda\theta/L$, where $\tau_r$, $\lambda$, $\theta$, and L denote the torque, restoring proportionally constant, tip deflection angle, and catheter length, respectively. In equilibrium, the magnetic torque, $\tau_B$, balances the restoring torque so that $\tau_B = mB \sin(\beta-\theta) = \lambda\theta/L$, where m, B, and $\beta$ are the tip's magnetic moment, the magnetic field strength, and the deflection angle of the magnetic field (which leads $\theta$). From this, four limitations for the Stereotaxis platform are noted which result in the need for a strong external magnetic field. First, more magnetic torque is required to deflect the catheter by greater angles. For example, testing has shown that for a 5-centimeter extension of a Stereotaxis catheter (i.e., measured backwards from the catheter's tip), a tangential force of 1 gram will deflect the catheter's tip by 20 degrees. However, nearly 6 grams are needed for a 120-degree deflection of the catheter's tip. Second, once $\beta$ leads $\theta$ by 90 degrees, no additional deflection is possible. As a result, Stereotaxis' catheters cannot be deflected beyond 120 degrees using 100 milli-tesla. Third, once $\beta$ equals 180 degrees, the deflection is unstable and the catheter can flip to the other side. Only by using additional sheaths can all directions be accessed while applying forces greater than 20 grams. Without the sheaths, only 6 grams of contact force is possible, which can be insufficient in conveying effective therapy. And fourth, because the catheter can twist, the magnetic force generated on the tip will pull the catheter out of the desired deflection plane. To counteract this, the Stereotaxis platform uses two magnets each weighing about 500 kilograms which are oppositely placed so that the magnetic field adds whereas the gradient subtracts.

There remains a need to develop improved magnetically-controlled catheter and sheath devices.

SUMMARY OF THE INVENTION

The present invention provides magnetically-controlled linkage-based devices yielding improved magnetically controlled catheters and sheaths. As opposed to expending energy to fight the catheter's restoring force, the present invention redesigns the catheter as a series of low friction linkages so that improved navigation and tissue contact are accomplished using low-strength magnetic fields. The invention results in greater catheter control and tissue contact using much smaller magnetic fields than previously possible. The magnetically-controlled linkage-based device provides an open internal lumen for electrical leads, fluids, and other elements conducive to the intended therapy.

One aspect of the present invention provides a magnetically controllable linkage based medical device for interventional medical procedures includes a magnetic tip subassembly including magnet elements thereon; a plurality of linkage body elements connected in sequence, a distal linkage body element coupled to the magnetic tip subassembly, wherein each linkage body element is configured for deflection in at least one deflection direction; a linkage base element coupled to a proximal linkage body element; a support body connected to the linkage base element; at least one pair of control wires passing within the support body, the linkage base element, and the linkage body elements to the magnetic tip subassembly; wherein the device is configured such that an externally-generated magnetic field deflects the magnetically-controlled linkage-based device in at least one deflection direction, and wherein selectively tensioning the control wires can hold the magnetically-controlled linkage-based device in a desired orientation. The device is configured such that the externally-generated magnetic field which deflects the magnetically-controlled linkage-based device is less than 40 millitesla.

One aspect of the present invention provides a method of magnetically controlling a linkage based medical device for interventional medical procedures, comprising the steps of: Providing a linkage based medical device having a magnetic tip subassembly including magnet elements thereon, a plurality of linkage body elements connected in sequence, a distal linkage body element coupled to the magnetic tip subassembly, wherein each linkage body element is configured for deflection in at least one deflection direction, a linkage base element coupled to a proximal linkage body element; and a support body connected to the linkage base element; and Deflecting the linkage body elements with an externally-generated magnetic field less than 40 millitesla to position the magnetically-controlled linkage-based device in a desired orientation.

One aspect of the present invention provides a magnetically controllable linkage based medical device for delivery of ablative therapy for the treatment of atrial fibrillation, the device comprising: a magnetic tip subassembly including magnet elements thereon; a plurality of linkage body elements connected in sequence, a distal linkage body element coupled to the magnetic tip subassembly, wherein each linkage body element is configured for deflection in at least one deflection direction; a linkage base element coupled to a proximal linkage body element; a support body connected to the linkage base element; and wherein the device is configured such that an externally-generated magnetic field of less than 25 millitesla deflects the magnetically-controlled linkage-based device in at least one deflection direction.

This invention describes new methods and devices relating to the control and design of magnetically-controlled linkage-based devices. In contrast to manual catheters navigated inside the body which possess a restoring force, low-friction linkage-based devices can be more-easily oriented and articulated. In addition, manual catheters possess a simple relationship between the deflection angle of the catheter and the catheter tip's orientation, which is not the case for linkage-based devices which offer more possibilities which yield the preferred tip orientation. However, efforts to manipulate linkage-based catheter-like devices using a few control wires have been hampered due to the wires forcing a one-to-one relationship between the device's deflection angle and the tip's orientation. To overcome this, more wires can be used to selectively create tension so that other orientations can be achieved; however, the added complexity reduces the ability to pass tools and therapeutic modalities through the inner lumen. This invention overcomes historical limitations by using an externally-generated magnetic field to encode space with magnetic information so that the magnets used in the construction of the magnetically-controlled linkage-based device orient in a way to minimize the total magnetic energy of the system. This methodology can be used to preferentially select the spatial configuration of the magnetically-controlled linkage-based device from all possible orientations of the device. As a result, lower external magnetic fields can be used to navigate the magnetically-controlled linkage-based device as compared to other methods. Furthermore, control wires can be used to control and/or sense the forces applied to the magnetically-controlled linkage-based device's tip due to contacting tissue. In the case of electrophysiology, better and safer tissue contact can be delivered for the purpose of delivering ablation therapy to treat arrythmias. Because the lumen of the magnetically-controlled linkage-based device remains open, other therapeutic modalities, devices, and tools can be passed to improve therapies.

These and other advantages of the present invention are set forth in the following description and associated figures.

DETAILED DESCRIPTION OF THE PREFERRED EMBODIMENTS

Figure 1:
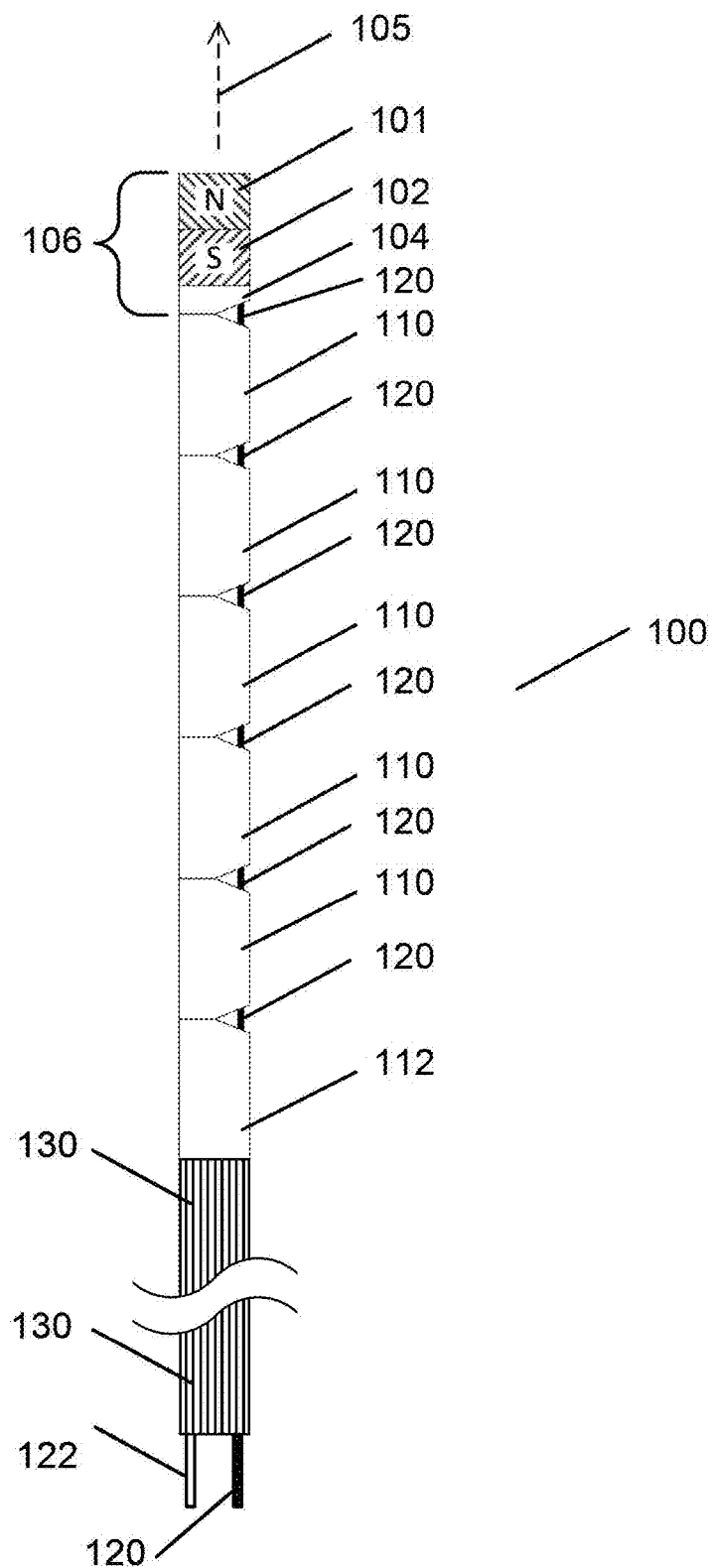
FIG. 1 is a drawing of an example of the magnetically-controlled linkage-based device according to one embodiment of the present invention possessing seven links and six open inner joints.

FIG. 1 is a drawing 100 of an example of the magnetically-controlled linkage-based device possessing seven links and six open inner joints (or equivalently, six closed outer joints). In this configuration, the magnetically-controlled linkage-based device is in a straight configuration with the magnetic tip subassembly 106 0-degrees from vertical. North and South magnet elements (101 and 102, respectively) are connected to the tip base 104 in this example. Together, the North and South magnet elements (101 and 102, respectively) and the tip base 104 comprise the magnetic tip subassembly 106. The magnetic tip subassembly 106 is connected to a linkage body element 110, which is connected to a sequence of additional four identical linkage body elements 110, with the last connected to the linkage base element 112. The linkage base element 112 is connected to a support body 130. An inner control wire 120 and an outer control wire 122 are passed within the support body 130, the linkage base element 112, and the linkage body elements 110 to the magnetic tip subassembly 106. An externally-generated magnetic field 105 is used to deflect the magnetically-controlled linkage-based device 100.

Pulling or retracting the outer control wire 122 straightens the magnetically-controlled linkage-based device 100, as is depicted. Pulling or retracting the inner control wire 120 causes the magnetically-controlled linkage-based device 100 to deflect in a clockwise-like motion. By releasing the tension on the inner and outer control wires (120 and 122, respectively), the externally-generated magnetic field 105 causes the magnetically-controlled linkage-based device 100 to orient so that the energy state of the device is minimized (which results in the depicted configuration). Once in this orientation, the inner and outer control wires (120 and 122, respectively) can be tensioned which holds the deflected orientation of the magnetically-controlled linkage-based device 100. Although the depiction of the magnetically-controlled linkage-based device 100 indicates that the North and South magnet elements (101 and 102, respectively) of the magnetic tip subassembly 106 are aligned with the axis of the magnetic tip subassembly 106, it may be useful in cases to use an alternative magnetization direction.

One example application relating to the magnetically-controlled linkage-based device of the present invention includes the delivery of ablative therapy for the treatment of atrial fibrillation. Cardiac arrhythmias are abnormal heart rhythms. Normal pacing is maintained by the heart's sinus node located in the upper right atrium. From there, electrical signal travel to the atrioventricular node (located between the two atria) and to the ventricles' muscles (via the His bundle).

Arrhythmias can result in rapid heart rates (tachycardia) or irregular contractions (fibrillations), with most being classified as atrial fibrillation (AF), ventricular fibrillation (VF), ventricular tachycardia (VT), atrial flutter (AFL), and supraventricular tachycardia (SVT). AF is the most common arrhythmia, with a prevalence of nearly 6,000,000 in the United States (US) alone. By 2030, it is expected that the US prevalence will exceed 12,000,000. AF is triggered by fibrillations within the atria, causing desynchronization between the heart's upper and lower chambers. AF results in nearly 130,000 US deaths each year, which are associated with acute ischemic stroke and heart failure. Because the atria do not fully expel blood during AF episodes, pooling blood can form a thrombus. When thrombus breaks free, ischemic stroke can result, thus explaining why AF victims have a 5-fold greater stroke risk. AF-related stroke is also associated with 2-fold greater mortality, worse outcomes, and higher hospital costs. AF also aggravates heart failure via known mechanisms that include loss of atrial systole and irregular and/or fast ventricular conduction. Of all arrhythmias, AF places the most strain on healthcare systems. Each year, there are more than 1,200,000 acute episodes in the US, which are expected to rise to 2,600,000 by 2030. This has resulted in more than 750,00 annual hospitalizations, which have been increasing exponentially since 2000. Medical and indirect costs currently are estimated as $24 billion and $7 billion, respectively, which are expected to reach $55 billion and $11 billion by 2035.

While not as common at AF, VT and VF are considered the most dangerous arrhythmias in that they are responsible for nearly 300,000 US deaths each year. For VT, tachycardia begins in one of the ventricles. If not promptly treated, VT often progresses to VF, a cardiac emergency in which the ventricles fibrillate ineffectively without producing a functional heartbeat. Brain damage and death can occur within minutes. The remaining arrhythmias are AFL and SVT and are not life-threatening. For AFL, the atria's waveform is abnormal and the beat is fast, however pacing is regular. SVT consists of atrioventricular nodal reentrant tachycardia (AVNRT) and atrial tachycardia (AT). For AVNRT, abrupt tachycardia episodes occur due to reentrant circuits confined to the AV node and peri-nodal atrial tissue. For AT, the atria's beat is fast but possesses a normal waveform.

First-line arrhythmia therapies rely on pharmacologic management to prevent blood clots, control the ventricle beating rate, and restore proper rhythm. Because antiarrhythmic drugs are associated with high failure rates (>35%) and increased long-term side effects, catheter ablation is increasingly used. In this, radiofrequency (RF) energy is passed through the catheter's tip which destroy abnormal tissues disrupting proper electrical signals. Other ablation technologies rely on the use of coolants to disrupt abnormal electrical signals. Catheter ablation has demonstrated superior efficacy over anti-arrhythmic drug therapy in several clinical trials and meta-analyses, with other studies supporting ablation as a first-line therapy. Between 2000 and 2013, use of catheter ablation increased 20% annually, with more than 500,000 procedures performed in the US alone. However, catheter ablation is not a cure for arrhythmias and recurrence rates remain high at high as 50% for AF at VT. Reasons for arrhythmias recurrence are not fully understood, but the ablation procedure's complexity is often cited as a factor. Catheter navigation is a difficult procedure and requires skilled electrophysiologists. Because ablative catheters rely on complex tension-wire schemes operated from a meter away, errors accumulate in the transmission of forces and torques. Despite the recent introduction of force-sensing catheters, catheter navigation and heart-wall contact remain suboptimal and can lead to recurrence, ineffective treatment, or injury.

The present invention's design of magnetically-controlled linkage-based devices represents a low friction system. In contrast to manual catheters navigated inside the body which possess a restoring force, low-friction linkage-based devices of the present invention can be more-easily oriented using a relatively weak external magnetic field. In addition, manual catheters possess a one-to-one relationship between the catheter's deflection angle and the catheter tip's orientation, which is not the case for linkage-based devices of the present invention which offer more spatial configurations which yield the desired catheter tip orientation. However, historical efforts to manipulate linkage-based catheter-like devices using a control wires have been hampered due to the control wires forcing a one-to-one relationship between the device's deflection angle and the tip's orientation, which is similar to the limitations inherent with commercial catheters. To overcome this limitation, additional wires can be used to selectively create tension so that other orientations can be achieved; however, the added complexity results in a reduction of the working lumen's size which reduces the ability to pass tools and therapeutic modalities through the inner lumen. This invention overcomes this limitation by using an externally-generated magnetic field to encode space with magnetic information so that the magnets used in the construction of the magnetically-controlled linkage-based device orient with respect to the magnetic field (and the corresponding magnetic gradient) in a way to minimize the total magnetic energy of the system, thereby resulting in the ability to control the magnetically-controlled linkage-based device using a lower external magnetic field than otherwise possible. This methodology can be used to preferentially select the preferred orientation of the magnetically-controlled linkage-based device from a range of possible spatial configurations. As a result, lower external magnetic fields can be used to navigate the magnetically-controlled linkage-based device as compared to other magnetic-control methods and devices. Furthermore, the control wires can be used to control and/or sense the forces applied to the device's tip transmitted by the contacting tissue. In the case of electrophysiology, better and safer tissue contact can be exerted for the purpose of delivering ablation therapy to treat arrythmias. Because the lumen of the magnetically-controlled linkage-based device remains open, other therapeutic modalities, devices, and tools can be passed to improve therapies.

As detailed in the following discussion, the present invention combines the strengths of magnet-based robotics with manually-deflectable catheters, resulting in a reduction in the strength of the external magnetic field needed to control the linkage-based device. By using a magnet-tipped linkage-based design of the invention, the restoring forces normally associated with catheters can be greatly reduced if not removed, thereby removing the need for the magnetic field to counteract these restoring forces. Linkage catheter concepts (magnetic and non-magnetic) have been described for nearly fifty years. Historically, control of individual linkages relied on complex systems consisting of dozens of wires and control of magnetic linkages relied on uniform magnetic fields which resulted in multiple degenerate states for the same tip angle. Both approaches were largely abandoned given that catheters could not be reliably navigated, and tissue contact forces could not be maintained. The proposed technology's advantage is the use of the external magnet's field and gradient to encode space so that the lowest magnetic energy state corresponds to the preferential catheter state. Because energy is not spent fighting the catheter's restoring force, better catheter navigation and tissue contact is possible using a smaller external magnetic field than previously possible. Another advantage is that catheter tip's contact force against the tissue can be controlled by changing the distance of the linkage device to the external magnet. Internal control wires bend the linkage device and enable the catheter's tip-generated force to be controlled, enable the catheter's tip-generated forces to be measured, and prevents the linkage-based device from collapsing when the magnetic field is removed. Unlike manual catheters whose deflection plane is changed by manually rotating the catheter from beyond the femoral access point, other control wires can be used to control or lock the rotation of plane in which the magnetically-controlled linkage-based device bends. By locking the plane, the external magnet can create the same deflection for any magnet placement in a hemisphere centered on the catheter.

In short, the magnetic force generated on the tissue is given by $F \approx m \nabla B$. By locking the magnetically-controlled linkage-based device's plane of rotation, the deflection plane can be specified regardless of the external magnet's orientation, where the magnetic field in this plane is defined as $B_\perp$ so that $F_\perp \approx m \nabla B_\perp$. So long as the magnetic gradient is increasing, tissue contact is maintained. In effect, the external magnet can be used to encode space with magnetic information which can be used to preferentially select the orientation of the magnetically-controlled linkage-based device. Within this encoded space, the magnets that are associated with the linkages of the magnetically-controlled linkage-based device will orient so that the total magnetic energy of the system is minimized.

Conventional magnetic resonance imaging (MRI), for which a uniform magnetic field is generated, is not able to control the magnetically-controlled linkage-based device described in this invention. The uniformity of the MRI's magnetic field results in a near-zero magnetic spatial gradient within the MRI's bore. While the tip of the magnetically-controlled linkage-based device will orient to align with the MRI's magnetic field direction, all configurations of the magnetically-controlled linkage-based device which result in the magnetically-controlled linkage-based device's tip being aligned with the MRI's uniform magnetic field yield the same total energy. Thus, a conventional MRI cannot be used to preferentially configure the spatial orientation of the magnetically-controlled linkage-based device. Furthermore, while the MRI's gradient coils are designed to encode space so that imaging is possible, the generated gradient is weak in terms of its magnetic magnitude and the gradient pulse is generated for a very short time (e.g., less than a second). As a result, the MRI's gradient coils cannot be used to effectively control the magnetically-controlled linkage-based device proposed herein.

For example, in the case of treating arrythmias using ablation for AF, the invention described herein provides the ability to access a greater volume of the heart. This is because the external magnet field is able to select any one of the possible orientations of the magnetically-controlled linkage-based device and is not constrained by a one-to-one relationship between the device's deflection angle and tip orientation, as is the case with other devices. As a result, better contact can be made against the heart wall, which reduces the likelihood of perforations or other injuries. In addition, because tip angle can be selected by the external magnetic field, better tip orientations against the heart wall can be achieved, which can improve the delivery of existing and new therapeutic modalities.

Further, in the present invention because the magnetic torque does not fight a restoring force, a relatively small, less than 40 millitesla, preferably less than 25 millitesla and generally approximately 20 millitelsa (although test devices effectively used 15 millitesla), can be used which reduces the size of the external magnet system compared to other commercial magnet systems sold by companies like Stereotaxis, Inc (which require about 100 millitesla to control their devices). As a result, the external magnet can be easily positioned out of the way of the x-ray system. To control the force applied against moving tissue (e.g., the heart's wall), the magnetically-controlled linkage-based device can be tensioned at the furthest extension so as to stiffen the magnetically-controlled linkage-based device. Resultingly, forces against the tissue are increased when the moving tissue surface contracts into the magnetically-controlled linkage-based device's tip. This ability to increase the force against the heart's wall may be helpful in delivering better ablation lesions.

Other therapies and diagnostic modalities that can be provided by the magnetically-controlled linkage-based device include, but are not limited to, cardiac mapping, radiofrequency ablation, cryocooling ablation, laser ablation, microwave ablation, thermal ablation, cardiac ablation for arrythmias, tumor ablation, tissue biopsy, fluid sampling, navigation of tortuous vasculature (including the aortic arch), navigation of lumens within the body, embolization of tumors and vascular malformations, simulation of tissue, recordings of tissue electrical signaling, drug delivery, implantation of cells, localized delivery of gene-therapy modalities, force measurements of tissue, navigation of brain parenchyma or cerebral spinal fluid, bronchial tube and esophagus access, navigation within the stomach, colon, or intestines, navigation within the kidney or urethra, navigation of the inner ear, Eustachian tubes, sinus and nasal passages, or vessels of the eye, navigation within the spinal column, and other surgical intervention (e.g., hernia, hysterectomy, gastric bypass, and other orthoscopic-enabled procedures).

The linkages comprising the magnetically-controlled linkage-based device may also be described as, but is not limited to, segments, joints, elements, structures, bodies, parts, or pieces. The magnetically-controlled linkage-based device may make use of one or more joints or pivots which allows the magnetically-controlled linkage-based device to achieve other orientations. The joint may be located between, but is not limited to, the linkage adjacent to the support lumen, between linkages, along the support lumen. To enable rotation about the joint, one or more control wires may be used to rotate the magnetically-controlled linkage-based device distal to the joint. Alternatively, or in conjunction, one or more magnets can be placed distal to the one or more joints whose magnetization is perpendicular to the neighboring joint's rotation axis. As opposed or in addition to using separate magnets, it is possible to compose the linkages or parts of the support lumen from magnetic materials. When the component of the external magnetic field which is perpendicular to the axis of the joint's (or pivot's) rotation differs from the magnetization direction of the magnets (or magnetized components), a torque will be induced on the portion of the magnetically-controlled linkage-based device distal to the joint. If the joint is allowed to rotate or move, additional catheter control in enabled. For example, if the magnetically-controlled linkage-based device is designed to bend in a single plane which is defined as the "deflection plane," the component of the external magnetic field which extends outside of the deflection plan will induce a torque that on the magnet element distal to the pivot. If the pivot is free to rotate, greater catheter control in enabled.

The magnetically controlled linkage catheter's design offers unique safety features. If a linkage improperly operates, the control wires can serve as tethers. When or if necessary, the control wires can be released which causes the linkage catheter to fall into a fully relaxed state, thereby allowing easy removal. It is possible to design the control wires so that they break under specific force loads, which limits the amount of force exerted on the tissue.

The linkages and the magnet tip subassembly of the magnetically-controlled linkage-based device may be composed of a range of materials which improve performance for the intended use. Construction materials include, but are not limited to, biocompatible materials, plastics, stainless steel, metal, gold, brass, copper, titanium and/or titanium allows (e.g., nickel titanium), platinum and/or platinum allows (e.g., platinum cobalt and platinum iron), polymers, polyimides, silicone, nylon, polyurethane, polyethylene terephthalate, latex, thermoplastic elastomers, biocompatible materials, hydrophobic or hydrophilic materials, or ceramics materials.

To prevent bodily fluids from entering the device, the magnetically controlled linkage device can incorporate collapsible films. Example biocompatible fluid barriers make use of, but are not limited to, silicon, polytetrafluoroethylene (PTFE), and expanded PTFE.

The open lumen of the linkage device allows the passage of a number of therapeutically useful materials and/or modalities, including, but not limited to, electrically-conducting wires, irrigation, optical components, radiofrequency components, guidewires, microcatheters, catheters, drugs, stem cells, embolization beads, stimulators, biopsy tools, delivery tools and needles for drugs (including genes and stem cells), force sensors, ultrasound components, cryo-cooling, localization sensors, fiberoptic cables, aspiration devices and mechanisms, brachytherapy tools, tissue and fluid sampling tools, imaging devices, tissue and bone fusion tools, and surgical intervention modalities and devices.

The control wires may be composed of, but not limited to, one or more of the following materials: polymers, plastics, metals, fibers, and electro-strictive materials. The material traits may be described as, but are not limited to, the following descriptors: elastic, nonelastic, flexible, semi-rigid, flexible, nonflexible, braided, single filament, conducting, biocompatible, hydrophobic, and/or hydrophilic.

Manipulation of the control wires may be described as, but are not limited to, the following: articulate, articulated, articulating, retract, retracted, retracting, pull, pulled, pulling, tension, tensioned, tensioning, relax, relaxed, relaxing, extend, extended, extending, push, pushed, pushing, withdraw, withdrawn, withdrawing, advance, advanced, and advancing. Manipulation of the linkages may be described as, but is not limited to, the following: bending, deflecting, orienting, configuring, angulating, articulating, rotating, positioning, repositioning, torqueing, swinging, and shifting.

It may be desired to articulate the magnetically-controlled linkage-based device outside of a single plane. For this, linkage elements maybe designed so that manipulation can occur in three dimensions, thereby enabling additional magnetically-controlled linkage-based device control. A controller may be used to control the magnetically-controlled linkage-based device where manipulations include, but are not limited to, advancement, retraction, rotation, tensioning, vibrating, and angulating.

Because the inner and outer control wires move in an opposite fashion where one control wire retracts as the other extends, it is possible to design a magnetically-controlled linkage-based device controller which balances the retraction of one control wire with the extension of the opposite control wire. For this, one or more motors can be used. The controller can also be used to apply tension simultaneously to the controls wires for the purpose of stiffening the magnetically-controlled linkage-based device. This ability can provide a way of changing the force applied by the contacting tissue to the magnetically-controlled linkage-based catheter's tip. The controller can also be used to remove tension simultaneously to the control wires for the purpose of relaxing the magnetically-controlled linkage-based device. In some cases, it may be beneficial to match the extension of one wire in length and the opposite wire in retracted by the same length. To accomplish this, the design of the magnetically-controlled linkage-based device may be designed so that articulation of one or more linkages yields the same amount of change in control wire displacement for the retracting control wire and the extending control wire. Alternatively, the wire controller may be designed to adapt to different changes in wire displacements between the inner and outer control wires given known wire displacement characteristics of the magnetically-controlled linkage-based device.

Because forces applied to the magnetically-controlled linkage-based device can be transmitted along the control wire, one or more of the control wires can be used sense or detect forces applied to the magnetically-controlled linkage-based device's tip. From this, wire controller algorithms can be used to adaptively apply desired forces to the tissue. In some cases, the applied forces are constant over time and in other cases a specific temporal force profile may be applied.

The wire controller may incorporate one or more control elements for locking, releasing, or controlling one or more articulating joints of the magnetically-controlled linkage-based device, which allows the magnetically-controlled linkage-based device to rotate or articulate to other orientations.

The wire controller may incorporate one or more control elements for delivering therapy via the magnetically-controlled linkage-based device, which include, but are not limited to, electrical, optical, ultrasound, radiofrequency modalities, irrigation, aspiration, tissue and fluid sampling, brachytherapy, drug delivery, stem cell and gene delivery, bone fusion, embolization bead delivery, nerve stimulation, cryocooling, and other surgical interventions.

The wire controller may incorporate one or more control elements for controlling additional tools within the lumen of the magnetically-controlled linkage-based device. These include, but are not limited to, control of guidewires, microcatheters, catheters, surgical tools, biopsy tools, fiberoptic devices, drug delivery applicators, needles, and localization sensors.

The magnetically-controlled linkage-based device may make use one or more materials which assist in localizing the magnetically-controlled linkage-based device. These include, but are not limited to, x-ray opaque markers, magnetic resonance imaging opaque markers, magnetometers, impendence-based location materials, and magnetism-based location materials.

The magnetically-controlled linkage-based device may make use of materials to improve magnetic control. Magnets may be placed as one or more locations along the magnetically-controlled linkage-based device to improve interactions with the magnetic field. The magnet tip subassembly and/or one or more linkages may be composed of magnetic materials which include, but are not limited to, neodymium-boron-iron, iron, samarium-cobalt, platinum-cobalt, platinum-iron, low-carbon iron, magnetic steel, and other polymeric and ceramic materials. In addition, the use of electrically-conducting coils can be used to create a magnetic moment. The direction of magnetization of the magnetically-controlled linkage-based device's linkages and/or the magnetically-controlled linkage-based device's tip may be in any direction and are not required to align with any specific direction with respect to the device's linkages and/or the device's tip. Platinum-containing materials tend to exhibit natural x-ray opacity. The direction of magnetization for the one or more magnets used with the magnetically-controlled linkage-based device will be oriented so as to improve magnetic control. Likewise, if the one or more of the magnetically-controlled linkage-based device's linkages are composed from magnetic materials, the direction of magnetization for the one or more magnetized linkages forming the magnetically-controlled linkage-based device will be oriented so as to improve magnetic control.

The magnetically-controlled linkage-based device may make use of materials to improve tissue contact at the tip of the magnetically-controlled linkage-based device. These include, but are not limited to, the use of one or more springs or spring-like materials which can help equalize, reduce, or increase the force applied to tissues.

The external magnet system for controlling the magnetically-controlled linkage-based device may be built from materials which generate a strong magnetic field. The external magnet system will be capable of generating the necessary magnetic field for controlling the magnetically-controlled linkage-based device. Magnets contained within the external magnet system may be composed from permanent magnetic materials, conducting magnets, or superconducting magnets. Articulation of the magnet may be used to ensure the required magnetic field are generated on the magnetically-controlled linkage-based device. Articulation may include one or more rotation components and one or more translational components. Actuation of the rotational and/or translational components may be performed with a beneficial temporal profile. For example, a changing magnetic field which matches the temporal characteristics of the heart may be used to impart the best force of the magnetically-controlled linkage-based device's tip against the heart's wall. For this purpose, frequencies between 1-Hertz and 3-Hertz are expected, although other frequencies may be employed. In other scenarios, it may be useful to use more than one magnet system, whose magnetic fields can be made to combine so as to improve overall control of the magnetically-controlled linkage-based device.

The external magnet system may make use of magnetic shielding which alters the extension of the magnetic field within the environment the external magnet system is placed. For example, magnetic shielding may be used near magnetically-sensitive implants, equipment, or tools. For magnet systems composed of permanent magnetic materials (which cannot be deactivated as is the case with conducting or superconducting magnets), shielding may be use when the magnet is stowed. This serves the purpose of effectively deactivating the magnet system when not in use or during transportation.

Figure 2:
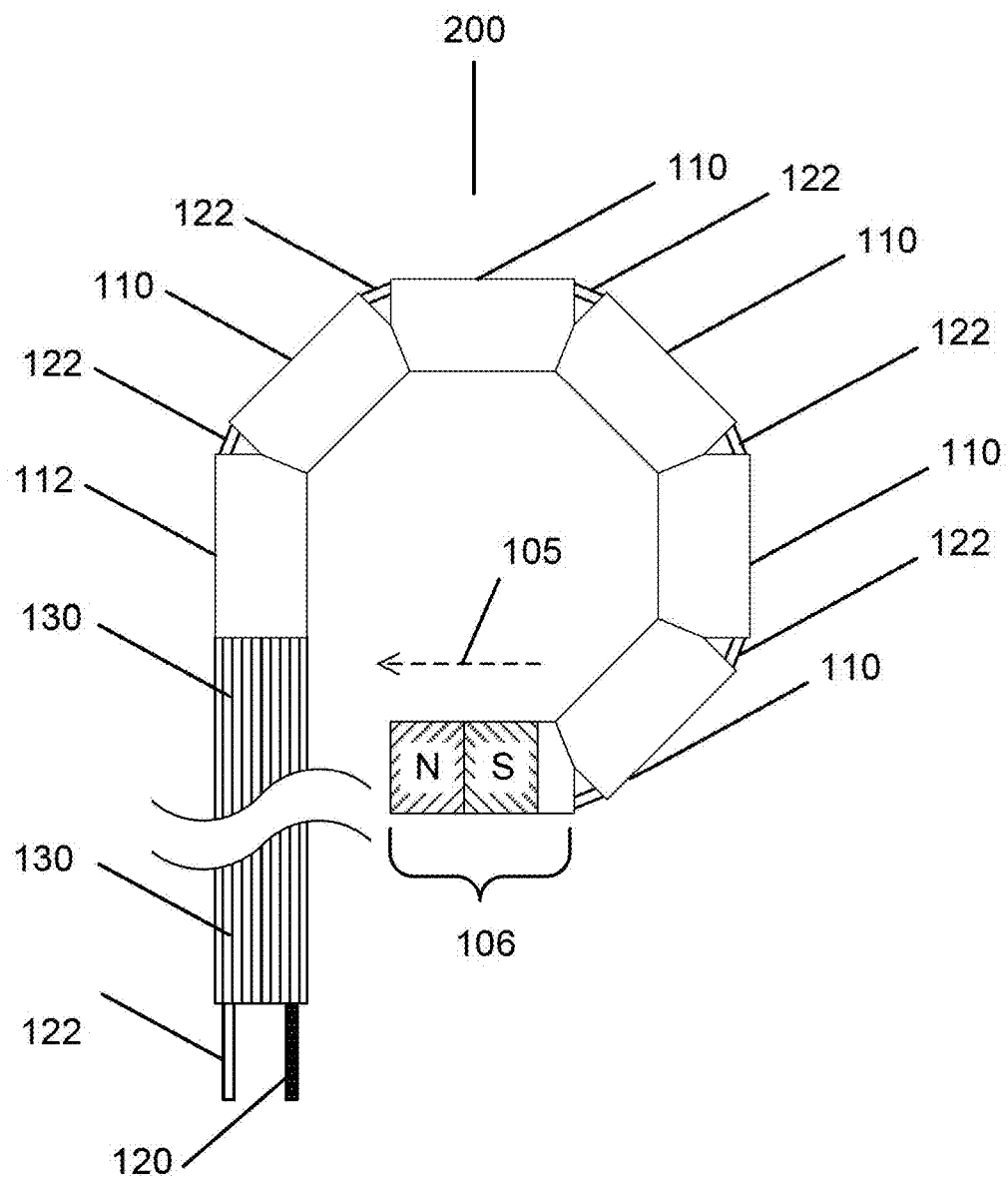
FIG. 2 is a schematic drawing of an example of the magnetically-controlled linkage-based device according to one embodiment of the present invention possessing seven links and six closed inner joints.

FIG. 2 is a drawing 200 of an example of the magnetically-controlled linkage-based device according to one embodiment of the present invention possessing seven links and six closed joints. In this configuration shown, the magnetically-controlled linkage-based device is in a fully-deflected configuration with the magnetic tip subassembly 106 270-degrees from vertical. The magnetic tip subassembly 106 is connected to a linkage body element 110, which is connected to a sequence of additional four identical linkage body elements, with the last connected to the linkage base element 112. The linkage base element 112 is connected to a support body 130. An inner control wire 120 and an outer control wire 122 are passed within the support body 130, the linkage base element 112, and the linkage body elements 110 to the magnetic tip subassembly 106. An externally-generated magnetic field 105 is used to deflect the magnetically-controlled linkage-based device 200. Pulling or retracting the outer control wire 122 straightens the magnetically-controlled linkage-based device 200. Pulling or retracting the inner control wire 120 causes the magnetically-controlled linkage-based device 200 to deflect in a clockwise-like motion, as is depicted. By releasing the tension on the inner and outer control wires (120 and 122, respectively), the externally-generated magnetic field 105 causes the magnetically-controlled linkage-based device 200 to orient so that the energy state of the device is minimized (which results in the depicted configuration). Once in this orientation, the inner and outer control wires (120 and 122, respectively) can be tensioned which holds the deflected orientation of the magnetically-controlled linkage-based device 200.

Figure 3:
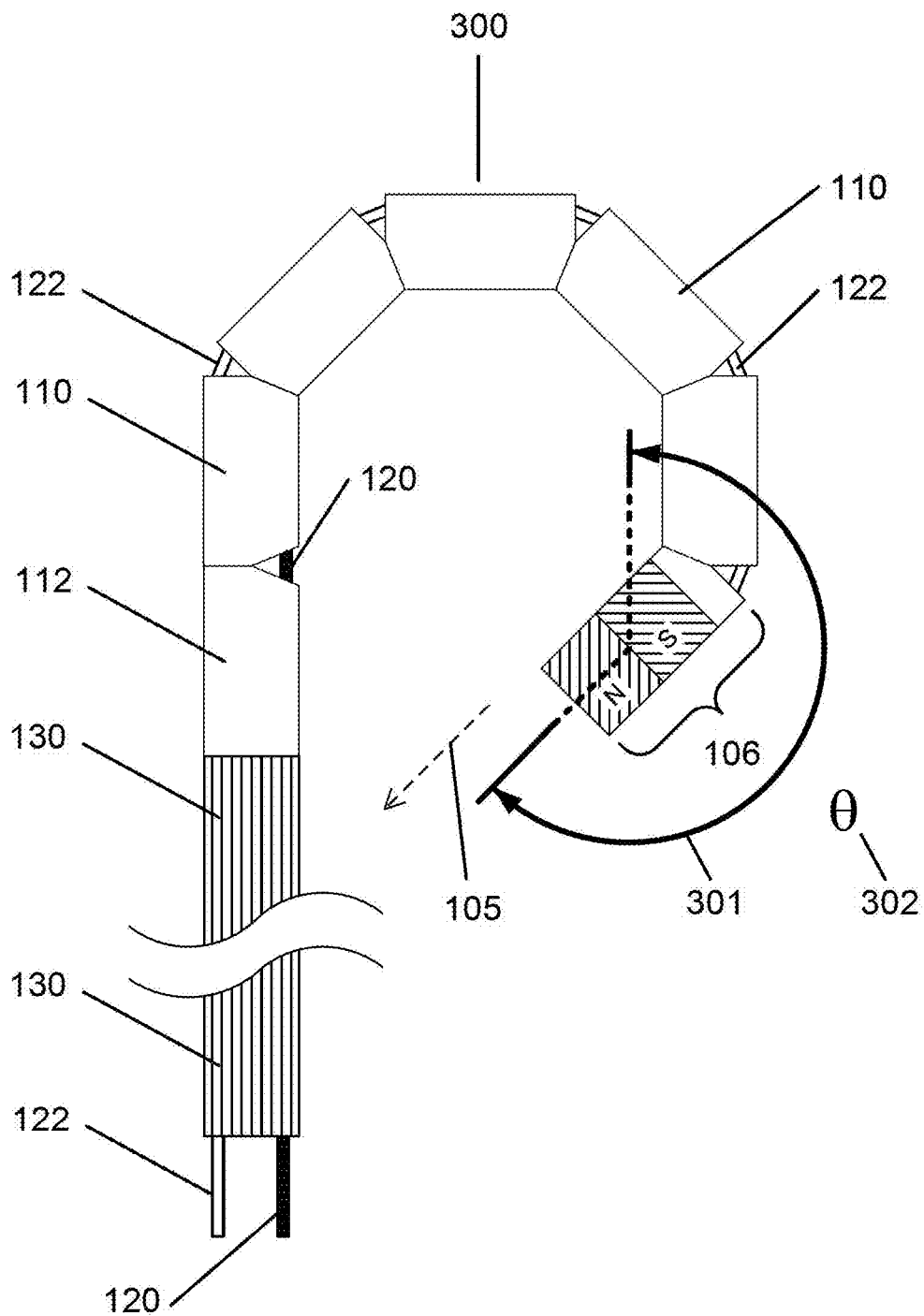
FIG. 3 is a schematic drawing of an example of the magnetically-controlled linkage-based device according to one embodiment of the present invention possessing seven links and six joints with one inner joint open and five inner joints closed.

FIG. 3 is a drawing 300 of an example of the magnetically-controlled linkage-based device according to another embodiment of the present invention and possessing seven links and six joints and shown with one inner joint open and five inner joints closed (or equivalently, with one outer joint closed and five outer joints open). In this configuration, the magnetically-controlled linkage-based device is in a partially-deflected configuration with the magnetic tip subassembly 106 225-degrees from vertical. The deflection of the magnetic tip subassembly 106 is represented by the deflection arc 301 and the angle theta (θ) 302. The magnetic tip subassembly 106 is connected to a linkage body element 110, which is connected to a sequence of additional four identical linkage body elements, with the last connected to the linkage base element 112. The linkage base element 112 is connected to a support body 130. An inner control wire 120 and an outer control wire 122 are passed within the support body 130, the linkage base element 112, and the linkage body elements 110 to the magnetic tip subassembly 106. An externally-generated magnetic field 105 is used to deflect the magnetically-controlled linkage-based device 300. In the depicted partially-deflected orientation, the inner joint between the linkage base element 112 and the neighboring inner joint of linkage element 100 is open with the remaining five inner joints closed (or equivalently, the neighboring outer joint of linkage element 100 is closed with the remaining five outer joints open). Pulling or retracting the outer control wire 122 straightens the magnetically-controlled linkage-based device 300. Pulling or retracting the inner control wire 120 causes the magnetically-controlled linkage-based device 300 to deflect in a clockwise-like motion, as is depicted. By releasing the tension on the inner and outer control wires (120 and 122, respectively), the externally-generated magnetic field 105 causes the magnetically-controlled linkage-based device 300 to orient so that the energy state of the device is minimized (where the minimized results in the depicted configuration). Once in this orientation, the inner and outer control wires (120 and 122, respectively) can be tensioned which holds the deflected orientation of the magnetically-controlled linkage-based device 300.

Figure 4:
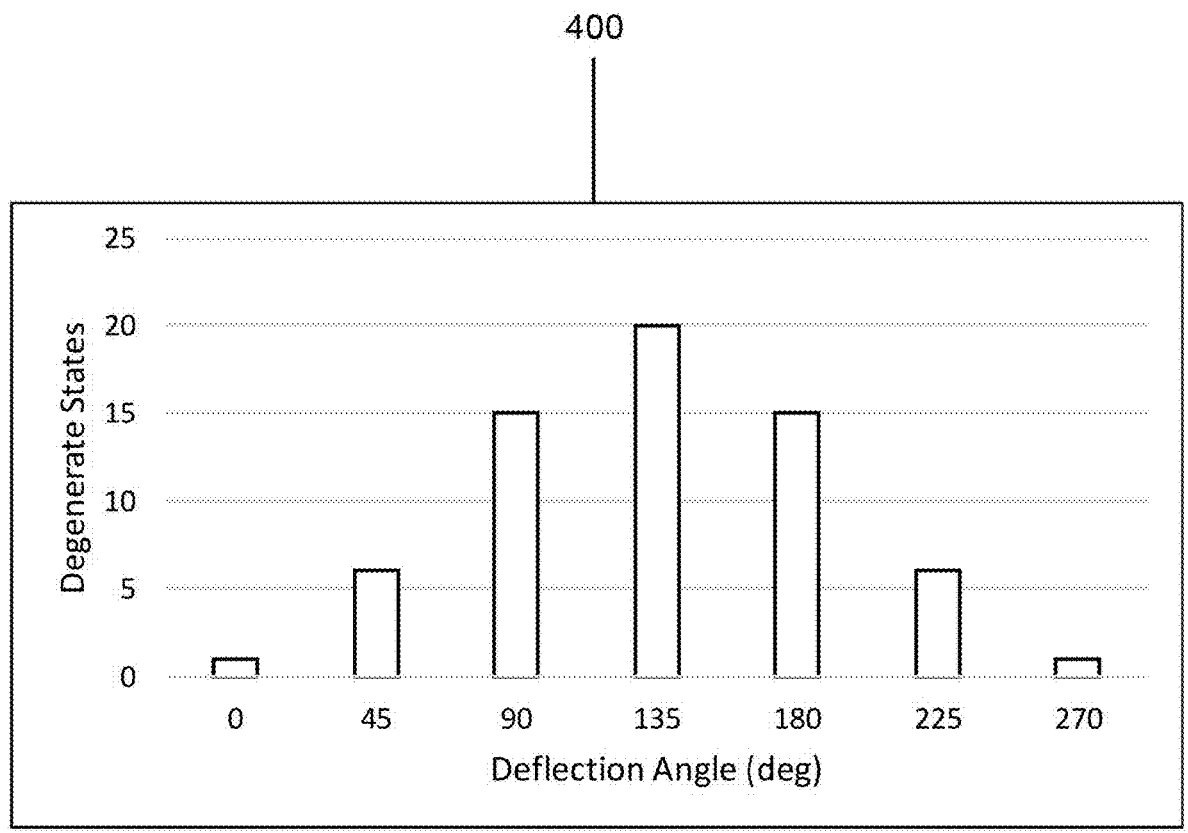
FIG. 4 is a drawing of the histogram detailing the number of possible states which results in a 225-degree deflection of the magnetic tip subassembly for a magnetically-controlled linkage-based device according to one embodiment of the present invention possessing seven links.

FIG. 4 is a drawing 400 of the histogram detailing the number of possible states which results in a 225-degree deflection of the magnetic tip subassembly 106 for a magnetically-controlled linkage-based device possessing seven links. Calculations show that for a 0, 45, 90, 135, 180, 225, and 270-degree deflections of the magnetic tip subassembly, there are 1, 6, 15, 20, 15, 6, and 1 possible configurations for the magnetically-controlled linkage-based device, respectively.

Figure 5:
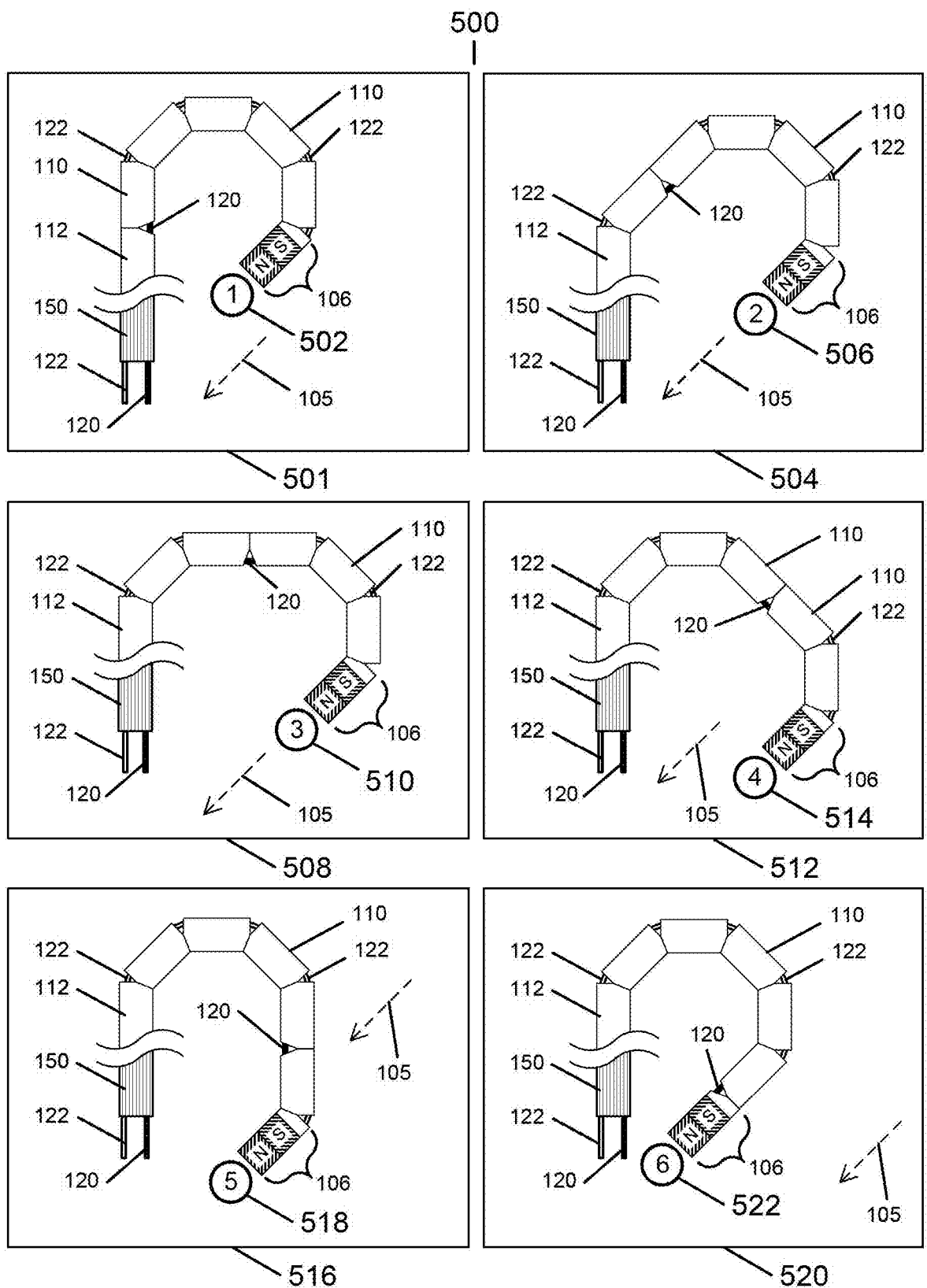
FIG. 5 is a schematic drawing of the six possible linkage device orientations which results in a 225-degree deflection of the magnetic tip subassembly using seven linkages and six joints according to one embodiment of the present invention.

FIG. 5 is a drawing 500 of the six possible linkage device orientations which results in a 225-degree deflection of the magnetic tip subassembly 106 using seven linkages and six joints. Subfigure 501 shows the depiction of the first of six possible linkage device orientations which results in a 225-degree deflection of the magnetic tip subassembly 106 using seven linkages and six joints. Symbol ("1") 502 represents the position of magnetic tip subassembly 106 for the open first inner joint from the linkage base element 112 with remaining inner joints closed (or equivalently, for the closed first outer joint from the linkage base element 112 with remaining outer joints open). Subfigure 504 shows the depiction of the second of six possible linkage device orientations which results in a 225-degree deflection of the magnetic tip subassembly 106 using seven linkages and six joints. Symbol ("2") 506 represents the position of magnetic tip subassembly 106 for the open inner second joint from the linkage base element 112 with remaining inner joints closed (or equivalently, for the closed second outer joint from the linkage base element 112 with remaining outer joints open). Subfigure 508 shows the depiction of the third of six possible linkage device orientations which results in a 225-degree deflection of the magnetic tip subassembly 106 using seven linkages and six joints. Symbol ("3") 510 represents the position of magnetic tip subassembly 106 for the open inner third joint from the linkage base element 112 with remaining joints closed (or equivalently, for the closed third outer joint from the linkage base element 112 with remaining outer joints open). Subfigure 512 shows the depiction of the fourth of six possible linkage device orientations which results in a 225-degree deflection of the magnetic tip subassembly 106 using seven linkages and six joints. Symbol ("4") 514 represents the position of magnetic tip subassembly 106 for the open inner fourth joint from the linkage base element 112 with remaining joints closed (or equivalently, for the closed fourth outer joint from the linkage base element 112 with remaining outer joints open). Subfigure 516 shows the depiction of the fifth of six possible linkage device orientations which results in a 225-degree deflection of the magnetic tip subassembly 106 using seven linkages and six joints. Symbol ("5") 518 represents the position of magnetic tip subassembly 106 for the open inner fifth joint from the linkage base element 112 with remaining joints closed (or equivalently, for the closed fifth outer joint from the linkage base element 112 with remaining outer joints open). Subfigure 520 shows the depiction of the sixth of six possible linkage device orientations which results in a 225-degree deflection of the magnetic tip subassembly 106 using seven linkages and six joints. Symbol ("6") 522 represents the position of magnetic tip subassembly 106 for the open inner sixth joint from the linkage base element 112 with remaining joints closed (or equivalently, for the closed sixth outer joint from the linkage base element 112 with remaining outer joints open). All six possibilities result in the same the magnetic tip subassembly 106 deflection angle. Without using the magnetic field 105 to encode space, pulling on the inner control wire 120 will tend to result in the sixth configuration 520, assuming there are no external forces and there is no friction within the linkage assembly. Additionally, assuming the inner and outer control wires, 120 and 122, respectively, are locked, forces applied to the magnetic tip subassembly 106 will result in the magnetic tip subassembly 106 moving to one or more of the other six configuration states (501, 504, 508, 512, 516). However, using the external magnetic field 105 to encode space so that the location of the magnetic tip subassembly 106 at or near the numbered symbols (502, 506, 510, 514, 518, 522) results in the lowest energy state for the magnetically-controlled linkage-based device assembly, it is possible to preferentially select any one of the six possible configuration (501, 504, 508, 512, 516, 520) which yields the same 225-degree deflection angle for the magnetic tip subassembly 106. Forces applied to the magnetic tip subassembly 106 which result in a displacement of the magnetic tip subassembly 106 while the magnetically-controlled linkage-based device is in the preferential low-energy configuration will result in the magnetic tip subassembly 106 being drawn back to the location associated with low or lowest energy. In any one of the six configurations, the inner and outer control wires (120 and 122, respectively) can be fixed, locked, or restricted so that the magnetic tip subassembly 106 can resist greater forces without displacing the magnetic tip subassembly 106.

Figure 6:
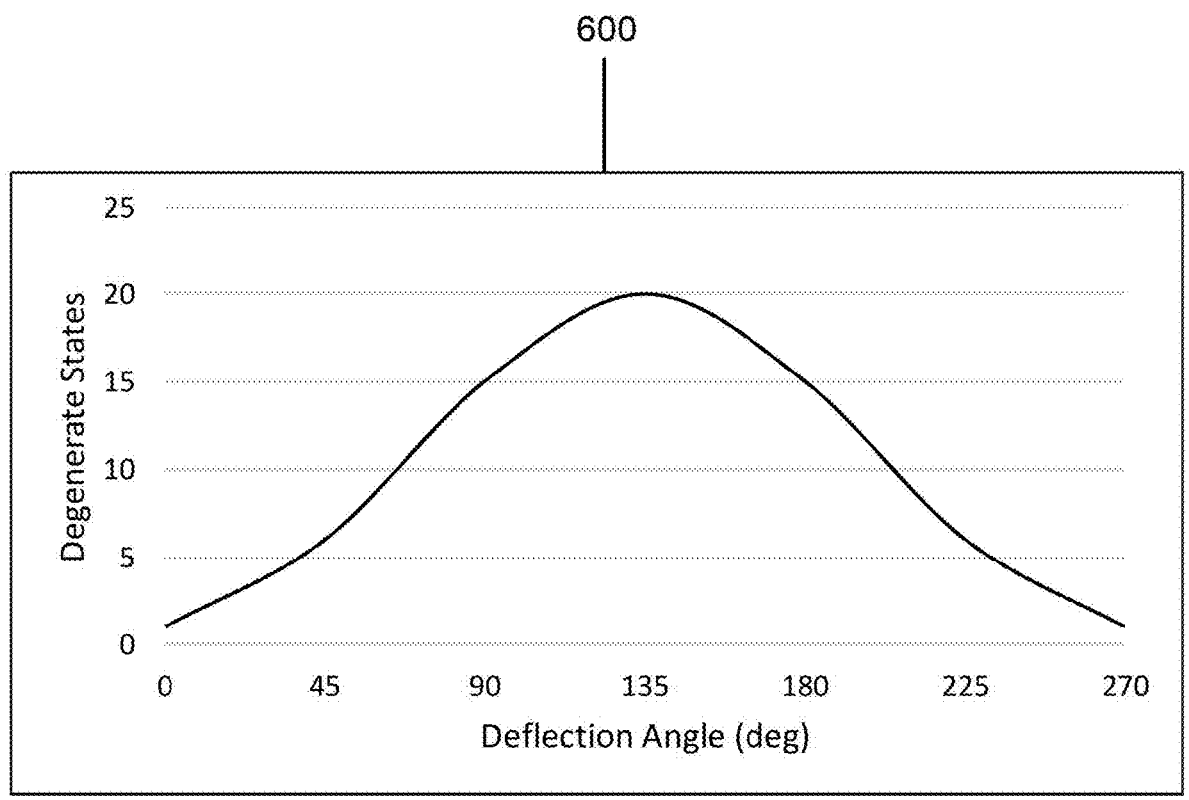
FIG. 6 is a graph of the distribution function detailing the number of possible states which results in a 225-degree deflection of the magnetic tip subassembly for a magnetically-controlled linkage-based device possessing seven links.

FIG. 6 is a drawing 600 of the distribution function detailing the number of possible states which results in a 225-degree deflection of the magnetic tip subassembly 106 for a magnetically-controlled linkage-based device possessing seven links. The distribution function assumes that inner joints between linkage elements of the magnetically-controlled linkage-based device can be partially open (or equivalently, that outer joints between linkage elements of the magnetically-controlled linkage-based device can be partially closed).

Figure 7:
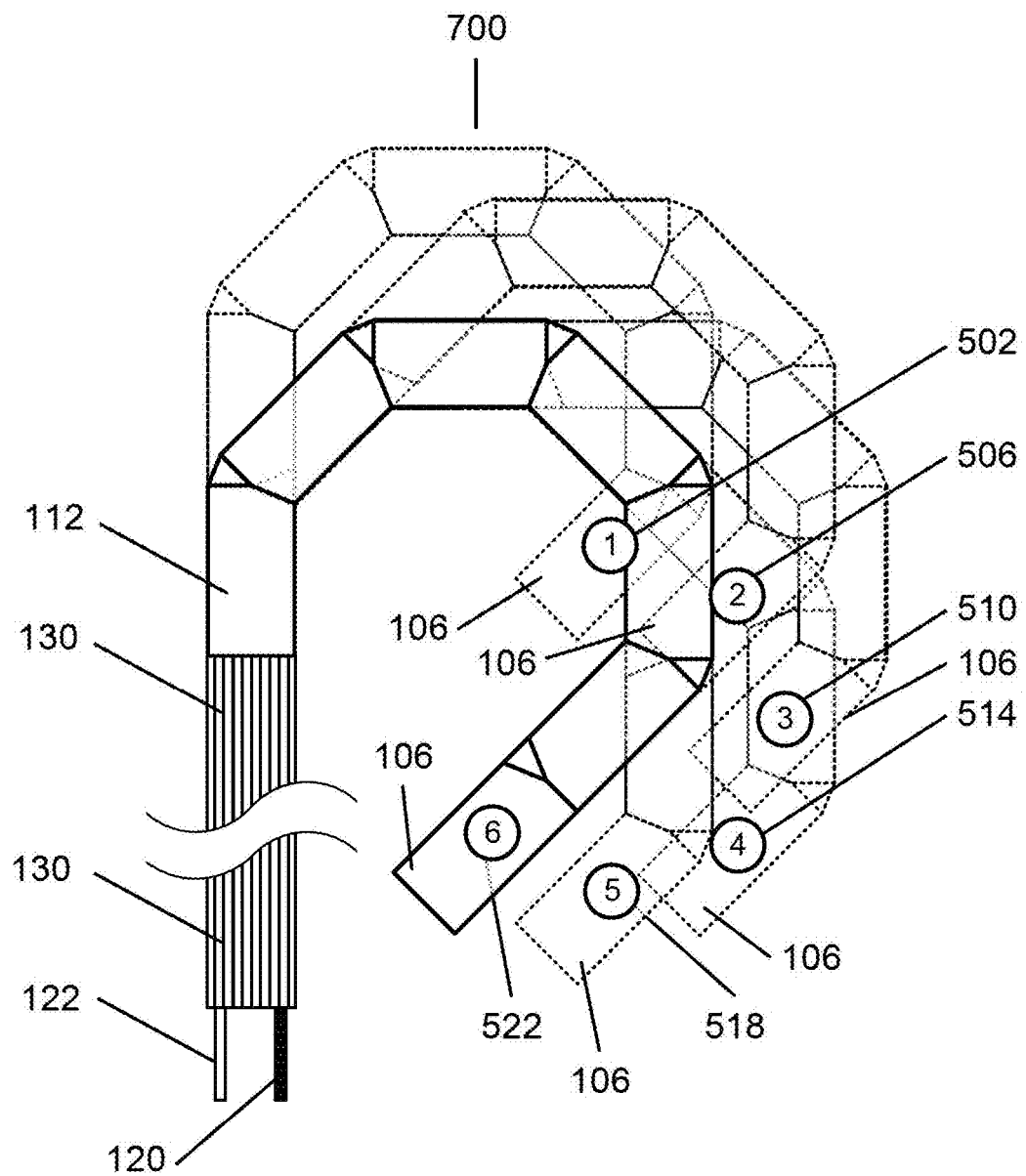
FIG. 7 is a schematic drawing overlaying all six possible locations of the magnetic tip subassembly using seven links and six joints with one inner joint open and five inner joints closed.

FIG. 7 is a drawing 700 overlaying all six possible locations of the magnetic tip subassembly 106 using seven links and six joints with one inner joint open and five inner joints closed (or equivalently, with one outer joint closed and five outer joints open). From the illustration, it can be seen that the six possible configurations of the magnetically-controlled linkage-based device are associated with unique locations. By encoding space with a magnetic field which minimizes the energy of the magnetically-controlled linkage-based device at or near one of the numbered symbols (502, 506, 510, 514, 518, 522), it is possible to preferentially select the magnetically-controlled linkage-based device configuration. It is also possible to extend or withdraw the support body 130 so that the spatial distribution of the possible locations for the magnetic tip subassembly 106 are further away or closer together. Fixing, locking, or restricting the inner and outer control wires (120 and 122, respectively) still allows the magnetically-controlled linkage-based device to reposition to one of the six locations identified by the numbered symbols (502, 506, 510, 514, 518, 522) regardless is a force is applied to the magnetic tip subassembly 106. If desired, the inner and outer control wires (120 and 122, respectively) can be further fixed, locked, or restricted so as to increase the friction against motion so that the preferential configuration of the magnetically-controlled linkage-based device can be reinforced against applied external or internal forces.

Figure 8:
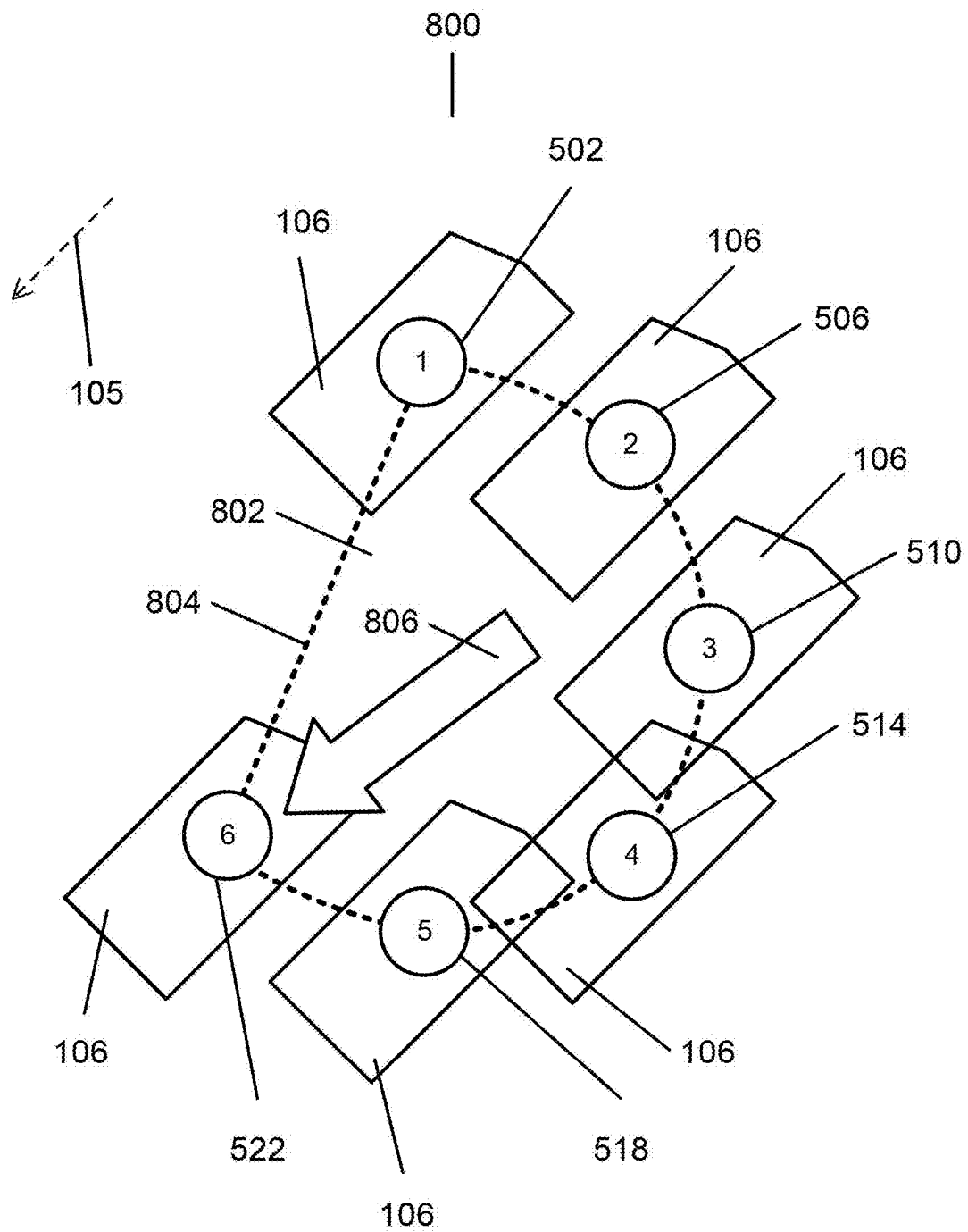
FIG. 8 is a schematic drawing of the range of possible magnetic tip subassembly positions using seven links and six joints and selection using magnetic energy minimization to select the best state.

FIG. 8 is a drawing 800 of the range of possible magnetic tip subassembly 106 positions using seven links and six joints and selection using magnetic energy minimization to select the best state. The six tip positions are the same as depicted in FIG. 7 which is a drawing 700 overlaying all six possible locations of the magnetic tip subassembly 106 using seven links and six joints with one inner joint open and five inner joints closed (or equivalently, with one outer joint closed and five outer joints open). By allowing the distance of the gap associate with a single open inner joint to be distributed across all six inner joints so that the total distances between gaps equals that of a single open inner joint (or equivalently, by allowing the summed distances of the gaps associated with the five open outer joints to be distributed across all six outer joints so that the total distances between the gaps equals that of the five open outer joints), the magnetic tip subassembly 106 can occupy any position within the magnet tip region 802, which is bound by the magnet tip region perimeter 804. Within this magnet tip region 106, a deflection angle of 225 degrees can be maintained for the magnetic tip subassembly 106. By encoding space with a magnetic field 105, it is possible to select the preferred spatial configuration of the magnetically-controlled linkage-based device given that the magnetically-controlled linkage-based device tends to occupy the lowest-energy configuration state. For the depicted example, the location identified by the symbol ("6") 522 corresponds to the lowest energy configuration of the magnetically-controlled linkage-based device which corresponds to the position of magnetic tip subassembly 106 for the open inner sixth joint from the linkage base element 112 with remaining joints closed (or equivalently, for the closed sixth outer joint from the linkage base element 112 with remaining outer joints open).

Figure 9:
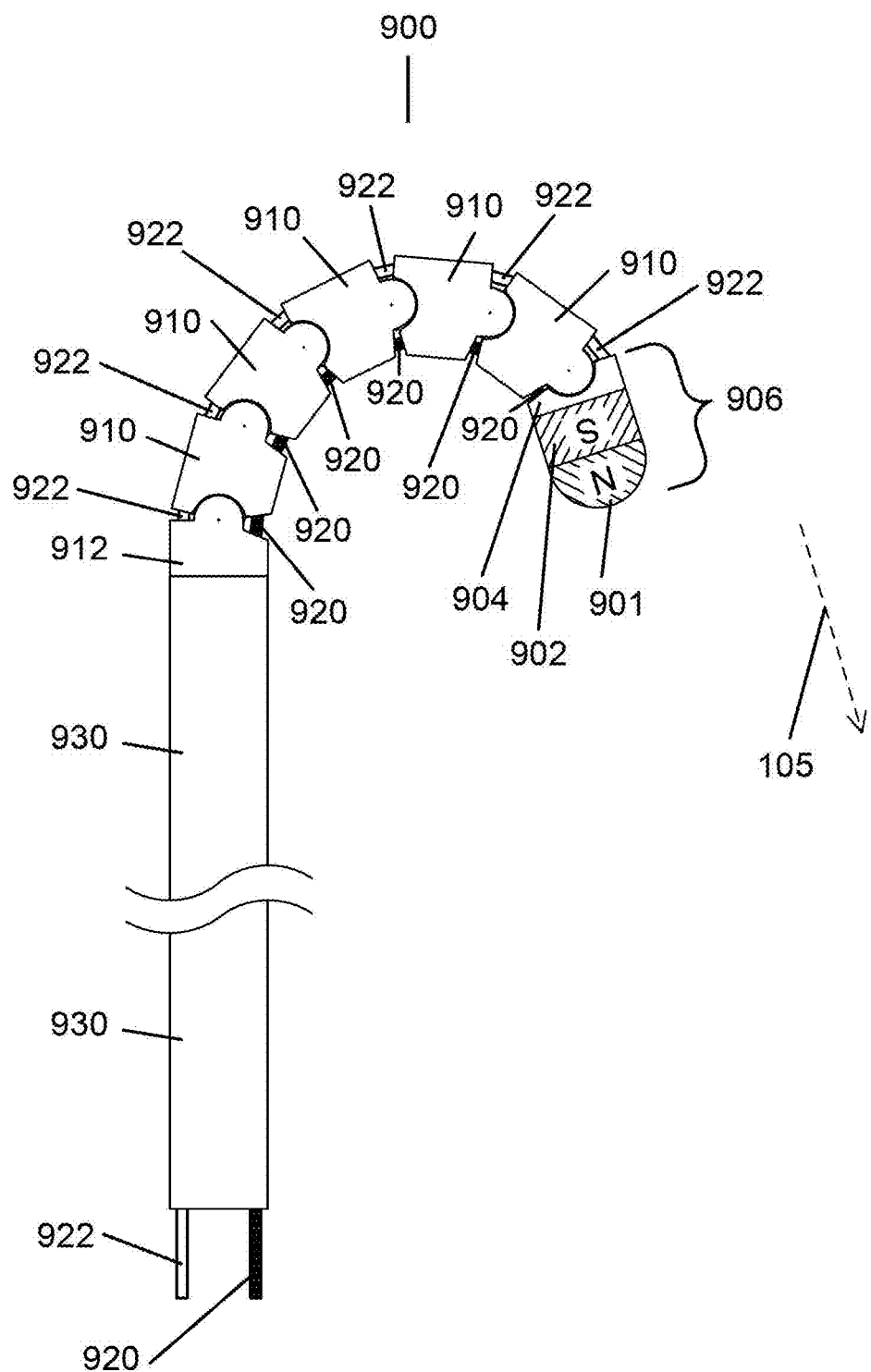
FIG. 9 is a schematic drawing of another example of the magnetically-controlled linkage-based device according to one embodiment of the present invention possessing seven links and six joints.

FIG. 9 is a drawing 900 of another example of the magnetically-controlled linkage-based device possessing seven links and six joints. North and South magnet elements (901 and 902, respectively) are connected to the tip base 004 in this example, which possesses a rounded tip on the North magnet element 901. Together, the North and South magnet elements (901 and 902, respectively) and the tip base 904 comprise the magnetic tip subassembly 906. The magnetic tip subassembly 906 is connected to a linkage body element 910, which is connected to a sequence of additional four identical linkage body elements, with the last connected to the linkage base element 912. The linkage base element 912 is connected to a support body 930. An inner control wire 920 and an outer control wire 922 are passed within the support body 930, the linkage base element 912, and the linkage body elements 910 to the magnetic tip subassembly 906. An externally-generated magnetic field 105 is used to deflect the magnetically-controlled linkage-based device 900. Pulling or retracting the outer control wire 922 straightens the magnetically-controlled linkage-based device 900. Pulling or retracting the inner control wire 920 causes the magnetically-controlled linkage-based device 900 to deflect in a clockwise-like motion. By releasing the tension on the inner and outer control wires (920 and 922, respectively), the externally-generated magnetic field 105 causes the magnetically-controlled linkage-based device 900 to orient so that the energy state of the device is minimized (which results in the depicted configuration). Once in this orientation, the inner and outer control wires (920 and 922, respectively) can be tensioned which holds the deflected orientation of the magnetically-controlled linkage-based device 900. Although the depiction of the magnetically-controlled linkage-based device 900 indicates that the North and South magnet elements (901 and 902, respectively) of the magnetic tip subassembly 906 are aligned with the axis of the magnetic tip subassembly 906, it may be useful in cases to use an alternative magnetization direction.

Figure 10:
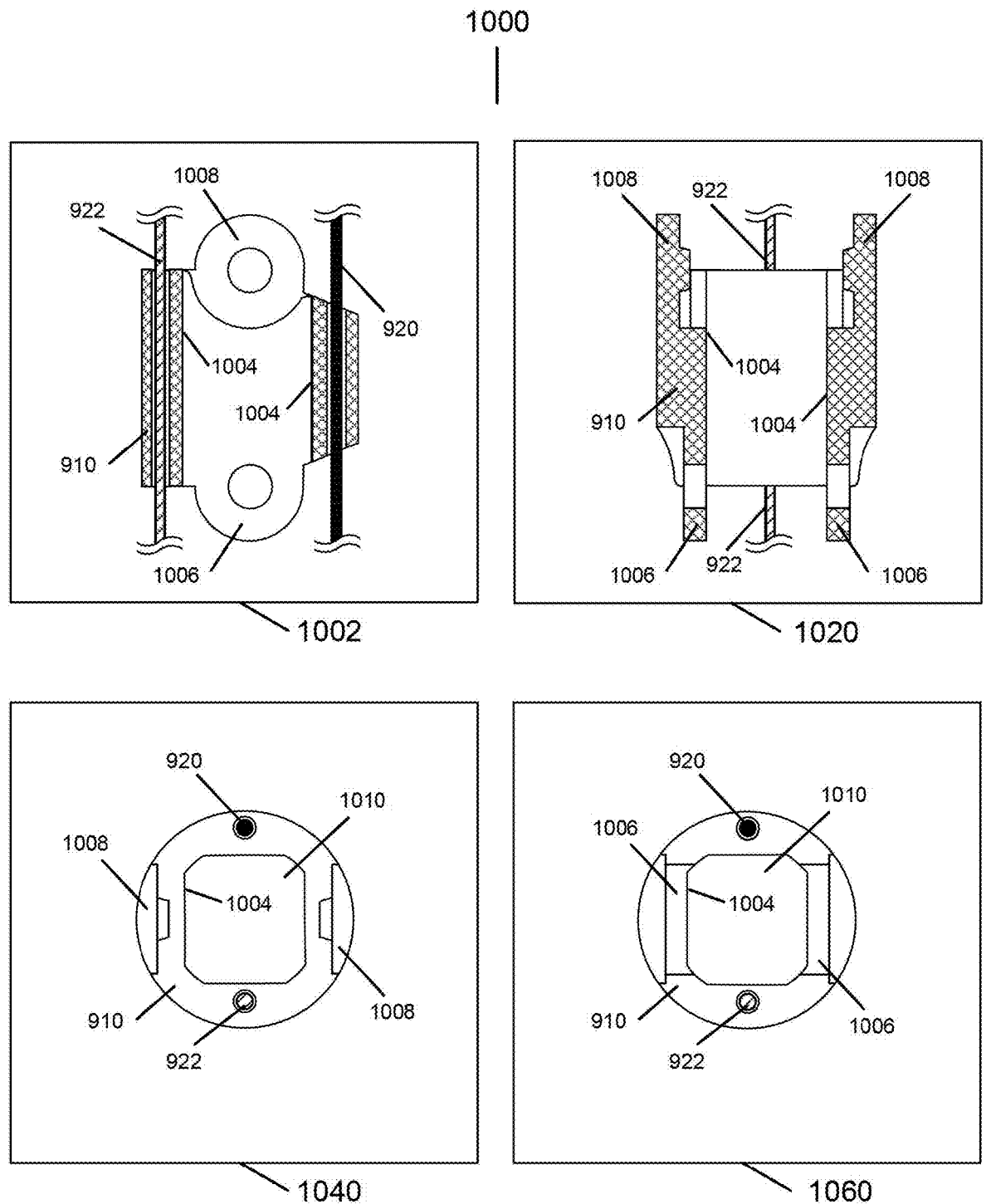
FIG. 10 is a drawing detailing the elements of a single linkage of the second example of the magnetically-controlled linkage-based device according to one embodiment of the present invention.

FIG. 10 is a drawing 1000 detailing the elements of a single linkage of the second example 900 of the magnetically-controlled linkage-based device. Subfigure 1002 shows the cross section of the linkage body element 910 with the inner and outer control wires shown (920 and 922, respectively). The inner linkage walls 1004 are shown, between which the region in open so that other tools, elements, and therapeutic modalities may be passed. An inner coupling element (or tab) 1006 and an outer coupling element (or tab) 1008 are shown, which allow connection of additional linkage elements. These inner and outer coupling elements (or tabs) (1006 and 1008, respectively) may be designed to impact a desired degree of friction between linkage elements, including the possibility of minimal friction. Subfigure 1020 shows another cross section of the linkage body element 910, taken traverse to the plane shown in subfigure 1000. From this viewing perspective, the outer control sire 922 is seen. Subfigure 1040 shows another cross section of the linkage body element 910, taken traverse to the planes shown in subfigures 1000 and 1020. From this viewing perspective, the outer coupling elements 1008 are seen, as are the inner and outer control wires (920 and 922, respectively). The inner linkage wall 1004 is shown which reveals an open region 1010 through which other tools, elements, and therapeutic modalities may be passed. Subfigure 1060 shows another cross section of the linkage body element 910, taken opposite from that of subfigure 1040. From this viewing perspective, the inner coupling elements 1006 are seen, as are the inner and outer control wires (920 and 922, respectively). The inner linkage wall 1004 is shown which reveals an open region 1010 through which other tools, elements, and therapeutic modalities may be passed.

Figure 11:
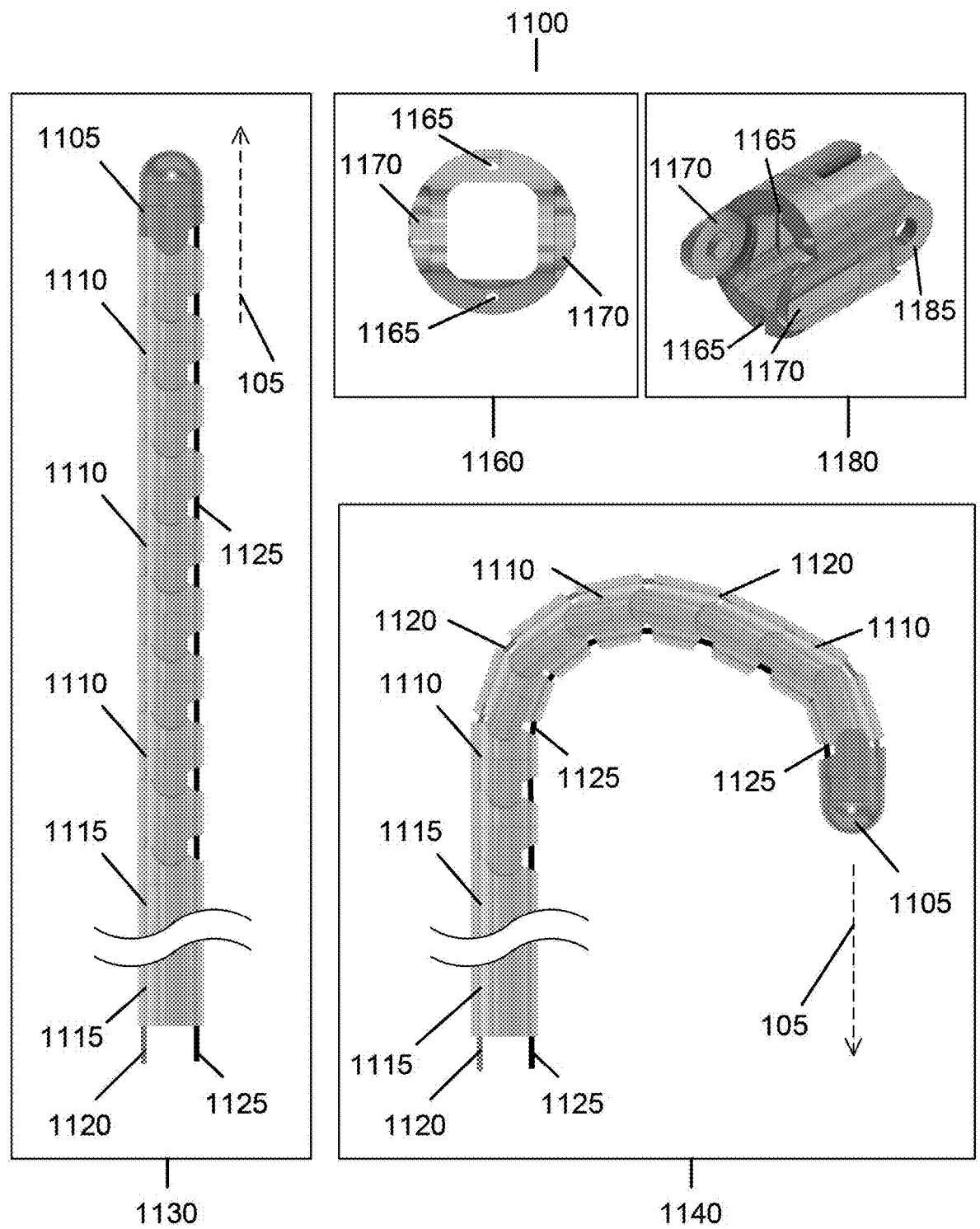
FIG. 11 is a drawing of another example of the magnetically-controlled linkage-based device according to one embodiment of the present invention possessing eleven links and ten joints.

FIG. 11 is a drawing 1100 of another example of the magnetically-controlled linkage-based device possessing eleven links and ten joints. Subfigure 1130 shows a depiction of the magnetically-controlled linkage-based device with eleven links and ten joints in a straight orientation. The linkage body elements 1110, the magnetic tip subassembly 1105, and the linkage base element 1115 are shown. The inner and outer control sires (1125 and 1120, respectively) and the external magnetic field 105 are also depicted. Subfigure 1140 shows a depiction of the magnetically-controlled linkage-based device with eleven links and ten joints in a straight configuration. Subfigure 1130 shows a depiction of the magnetically-controlled linkage-based device with eleven links and ten joints in a deflected configuration. Subfigure 1160 shows a depiction of the linkage's open lumen with the outer coupling elements 1170 and the openings for the inner and outer control wires 1165 visible. Subfigure 1180 shows a depiction of an isometric view of the linkage element 1110. From this perspective, the inner and outer coupling elements are visible (1185 and 1170, respectively).

COMPARATIVE EXAMPLE

Figure 12:
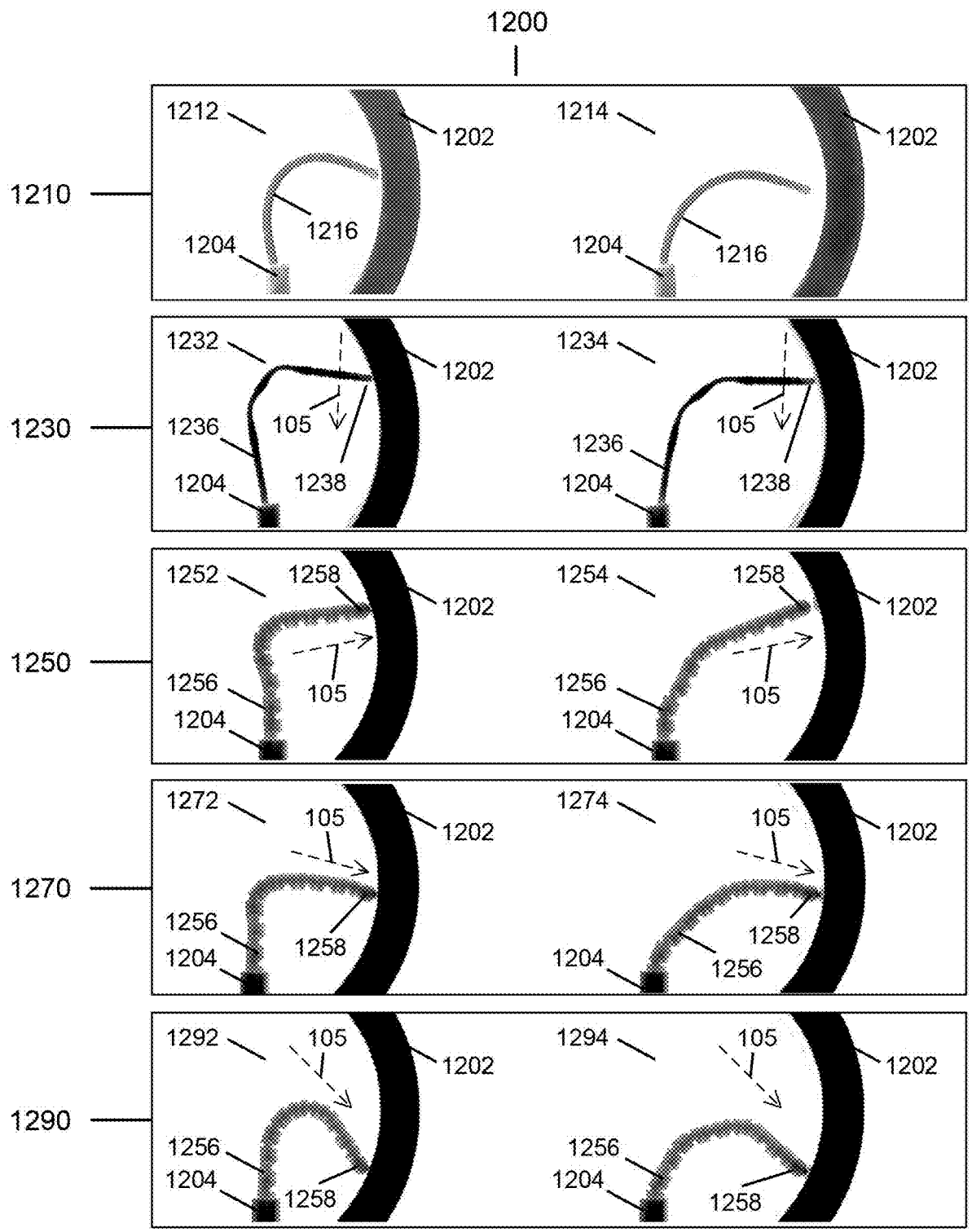
FIG. 12 are a collection of images depicting better control of an magnetically-controlled linkage-based device prototype according to one embodiment of the present invention as compared to commercially-manufactured manual and magnetically-controlled devices.

FIG. 12 are a collection of images 1200 depicting the better control of a magnetically-controlled linkage-based device prototype formed according to the principles of the present invention as compared to commercially-manufactured manual and magnetically-controlled devices. All devices were secured to a base 1204. For these studies, a motor-driven beating-heart model was built to assess navigational control and heart wall phantom 1202 contact, which reproduced a sixty beat-per-minute heartbeat. For the externally-generated magnetic field 105, a permanent magnet system was constructed which generated 15-millitesla about 10 cm from the external magnet's closest surface.

Subfigure 1210 depicts the performance of the J&J Navistar manual ablation device 1216 for the closest 1212 and furthest 1214 travel of the heart wall phantom 1202 (left and right images, respectively). As is shown, the J&J Navistar manual ablation device 1216 loses contact with the heart wall phantom 1202 at the furthest extension 1214 of the heart wall phantom 1202. Subfigure 1230 depicts the performance of the J&J RMT Navistar magnetic ablation device 1236 for the closest 1232 and furthest 1234 travel of the heart wall phantom 1202 (left and right images, respectively). The direction of the external magnetic field 105 is indicated, which generates a magnetic torque on the J&J RMT Navistar magnetic ablation device's magnetic tip 1238, which is magnetized is the direction of the J&J RMT Navistar magnetic ablation device's tip. Because the external magnetic field 105 is ninety degrees to the orientation of the J&J RMT Navistar magnetic ablation device's magnetic tip 1238 magnetization, the magnetic torque is maximized and no further tip deflection from the vertical axis is possible for either the closest or furthest extension of the heart wall phantom 1202 (1232 and 1234, respectively).

Subfigures 1250, 1270, and 1290 depicts the performance of the magnetically-controlled linkage-based device prototype 1256 for three directions of the external magnetic field. The magnetically-controlled linkage-based device prototype was composed of twelve linkage elements and used copolymer filament for the control wires and possessed a small magnet in the magnet tip subassembly 1258 with the magnetization directed along the central axis of the magnet tip subassembly 1258.

In subfigure 1250, the magnet tip subassembly 1258 is aligned with the external magnetic field 105 which is oriented about 80 degrees from the vertical access, and there is no loss of contact with the heart wall phantom for the closest or furthest extension of the heart wall phantom 1202 (1252 and 1254, respectively).

In subfigure 1270, the magnet tip subassembly 1258 is aligned with the external magnetic field 105 which is oriented about 120 degrees from the vertical access, and there is no loss of contact with the heart wall phantom for the closest or furthest extension of the heart wall phantom 1202 (1272 and 1274, respectively).

In subfigure 1290, the magnet tip subassembly 1258 is aligned with the external magnetic field 105 which is oriented about 160 degrees from the vertical access, and there is no loss of contact with the heart wall phantom for the closest or furthest extension of the heart wall phantom 1202 (1292 and 1294, respectively).

The results of this work support that the depicted magnetically-controlled linkage-based device prototype 1256 achieves better contact with the heart wall phantom 1202 than a J&J Navistar manual device 1216 and a J&J RMT Navistar magnetic device 1236. For the J&J Navistar manual device 1216, the study shows a loss of contact with the heart wall phantom 1202. Contact can only be retained by increasing the J&J Navistar manual device's 1216 insertion length from the base 1204, which adversely changes the contact angle. The J&J RMT Navistar device 1236 maintained heart-wall phantom 1202 contact, but could not deflect beyond about 95 degrees from the vertical axis using about 15 millitesla for the external magnetic field 105, with the external magnetic field 105 oriented by 90 degrees so that the magnetic torque generated on the J&J RMT Navistar device's magnet tip 1238 was maximized. Increasing the angle of the external magnetic field 105 greater than 180 degrees resulting in the J&J RMT Navistar device flipping to the other side. In contrast, the magnetically-controlled linkage-based device prototype 1256 successfully accessed all heart wall phantom 1202 locations (1252, 1254, 1272, 1274, 1292, and 1294) and maintained contact using an external magnetic field 105 of about 15 millitesla. In all cases, the magnetically-controlled linkage-based device prototype's magnet tip subassembly 1258 was closely aligned with the external magnetic field 105.

Figure 13:
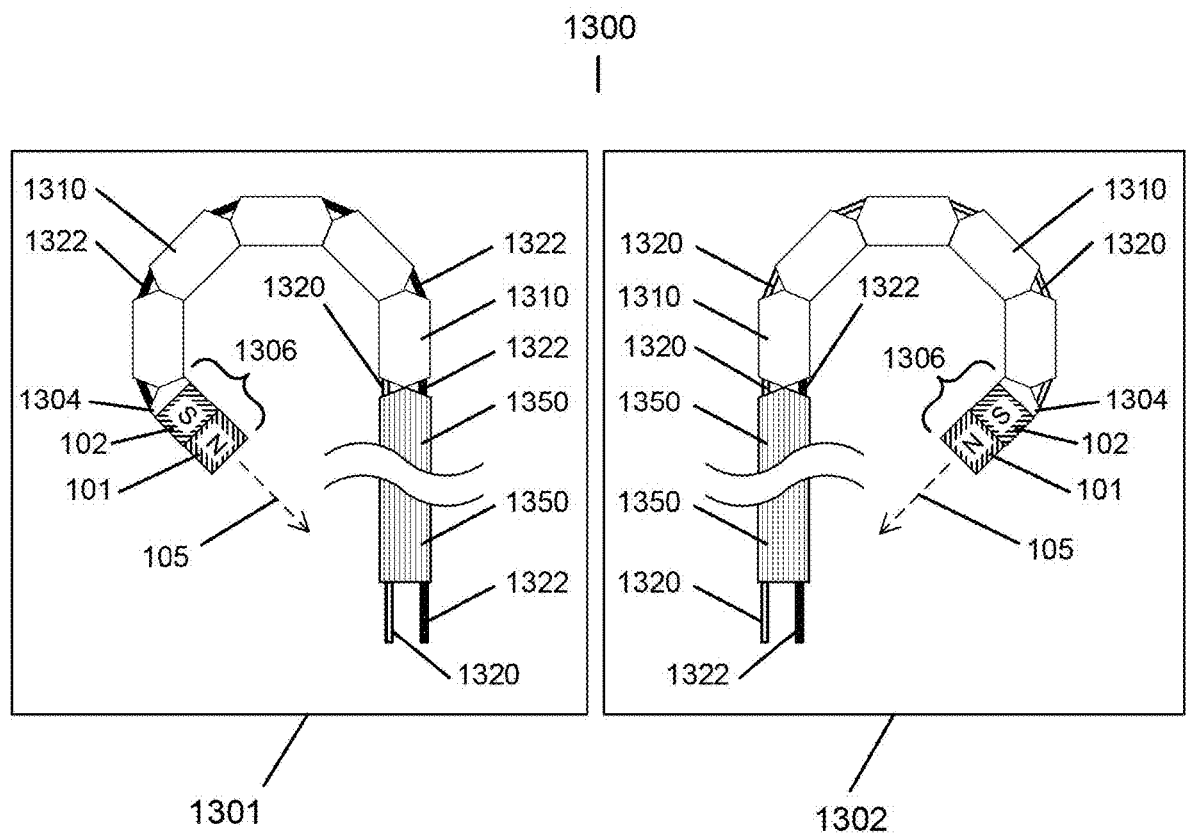
FIG. 13 is a drawing of another example of the magnetically-controlled linkage-based device possessing seven linkages and six joints which can deflect in two directions.

FIG. 13 is a drawing 1300 of another example of the magnetically-controlled linkage-based device possessing seven linkages and six joints which can deflect in two directions. Subfigure 1301 shows a counterclockwise deflection of the bidirectional magnetically-controlled linkage-based device. Subfigure 1302 shows a clockwise deflection of the bidirectional magnetically-controlled linkage-based device. North and South magnet elements (101 and 102, respectively) are connected to the bidirectional tip base 1304 in this example. Together, the North and South magnetic elements and the bidirectional tip base form the bidirectional magnet tip subassembly 1306. The bidirectional linkage elements are indicted by 1310, for which the depictions in 1301 and 1302 show five other bidirectional linkage elements 1310. The linkage elements 1310 are connected to a bidirectional linkage base element 1350. Two control wires (1320 and 1322) are shown which deflect the magnetically-controlled linkage-based device. By retracting or pulling the right control wire 1322, the magnetically-controlled linkage-based device deflects in a clockwise-like manner as is depicted in subfigure 1302. By retracting or pulling the left control wire 1320, the magnetically-controlled linkage-based device deflects in a counterclockwise-like manner as is depicted in subfigure 1301. By releasing the tension on the two control wires (1320 and 1322), the externally-generated magnetic field 105 causes the magnetically-controlled linkage-based device to orient so that the energy state of the device is minimized. For subfigure 1301, the lowest energy configuration of the magnetically-controlled linkage-based device corresponds to a magnetic field direction of about 135 degrees from the vertical axis. For subfigure 1302, the lowest energy configuration of the magnetically-controlled linkage-based device corresponds to a magnetic field direction of about 225 degrees from the vertical axis. Once in either orientation depicted in subfigures 1301 or 1302, the two control wires (1320 and 1322) can be tensioned which holds the deflected orientation of the magnetically-controlled linkage-based device. Although the depictions of the magnetically-controlled linkage-based device in subfigures 1301 and 1302 indicate that the North and South magnet elements (101 and 102, respectively) of the magnetic tip subassembly 1306 are aligned with the axis of the bidirectional magnetic tip subassembly 1306, it may be useful in cases to use an alternative magnetization direction.

Figure 14:
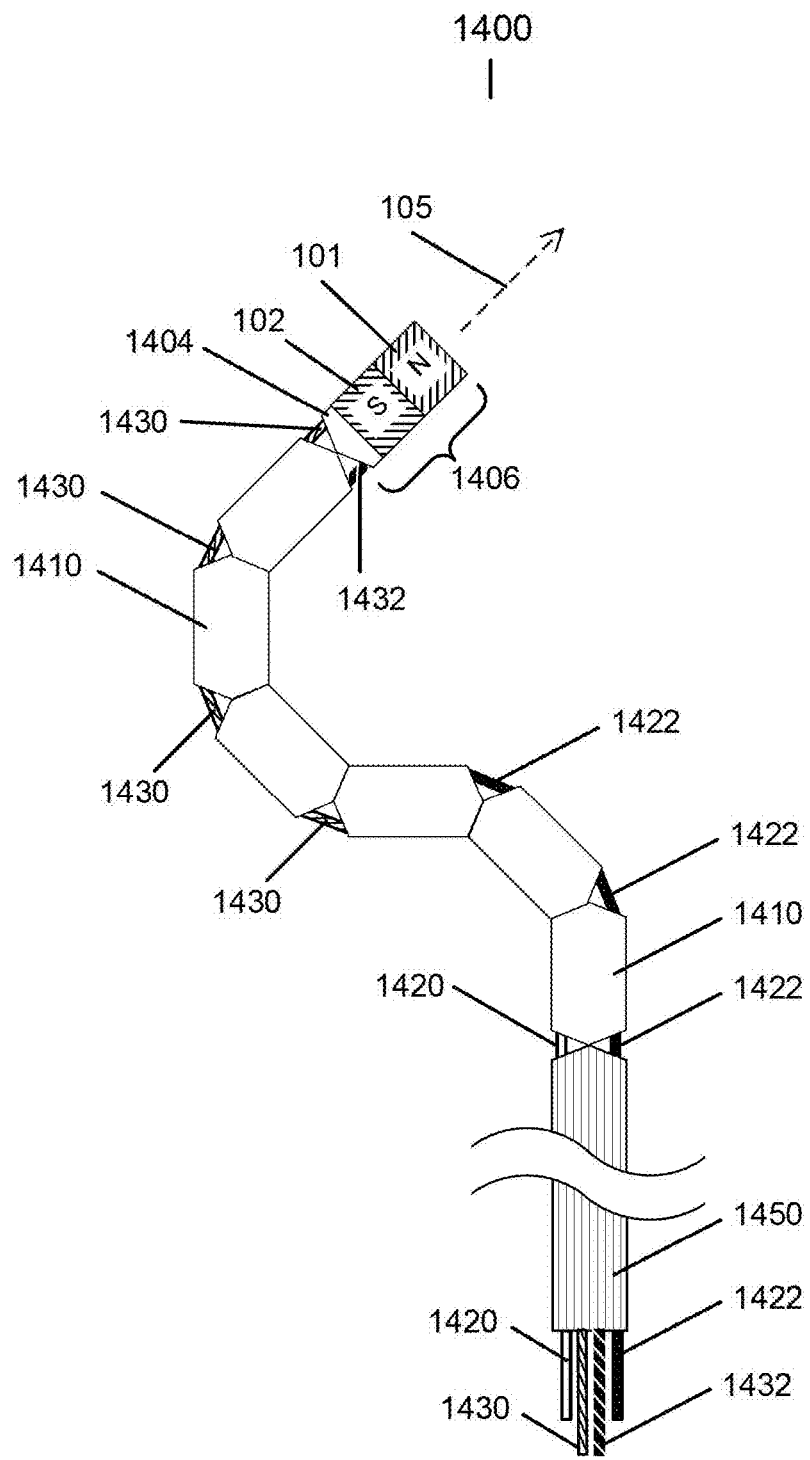
FIG. 14 is a drawing of another example of the magnetically-controlled linkage-based device according to one embodiment of the present invention possessing eight linkages and seven joints which possesses two degrees of control using four control wires.

FIG. 14 is a drawing 1400 of another example of the magnetically-controlled linkage-based device possessing eight linkages and seven joints which possesses two degrees of control using four control wires. North and South magnet elements (101 and 102, respectively) are connected to the bidirectional tip base 1404 in this example. Together, the North and South magnetic elements and the bidirectional tip base form the bidirectional magnet tip subassembly 1406. The bidirectional linkage body elements are indicted by 1410, for which a total of six linkage body elements 1410 are connected. The linkage body elements 1310 are connected to a bidirectional linkage base element 1450. Four control wires (1420, 1422, 1430, 1432) are shown. Two control wires 1420 and 1422 control the deflection and the ability to hold the three linkage body elements 1410 from the linkage base element 1450. Two other control wires 1430 and 1432 control the deflection and the ability to hold the three linkage body elements 1410 closest to the bidirectional magnet tip subassembly 1406.

By retracting or pulling control wire 1420, which controls the three linkage body elements 1410 closest to the linkage base element, while retracting or pulling control wire 1432, which controls the three linkage body elements closest to the bidirectional magnet tip subassembly 1406, while also applying a magnetic field 105 which encodes space so that the desired orientation of the bidirectional magnet tip subassembly 1406 is achieved (via a process of minimizing the energy associated with the magnetically-controlled linkage-based device's configuration), it is possible to achieve the shape depicted in 1400. The four control wires (1420, 1422, 1430, 1432) can be immobilized or locked or held or tensioned so that the magnetically-controlled linkage-based device configuration is more-securely held in the configuration depicted in 1400. Although the North and South magnet elements (101 and 102, respectively) of the bidirectional magnetic tip subassembly 1406 are aligned with the axis of the bidirectional magnetic tip subassembly 1406, it may be useful in cases to use an alternative magnetization direction or to use other magnets placed along the body of the magnetically-controlled linkage-based device.

Figure 15:
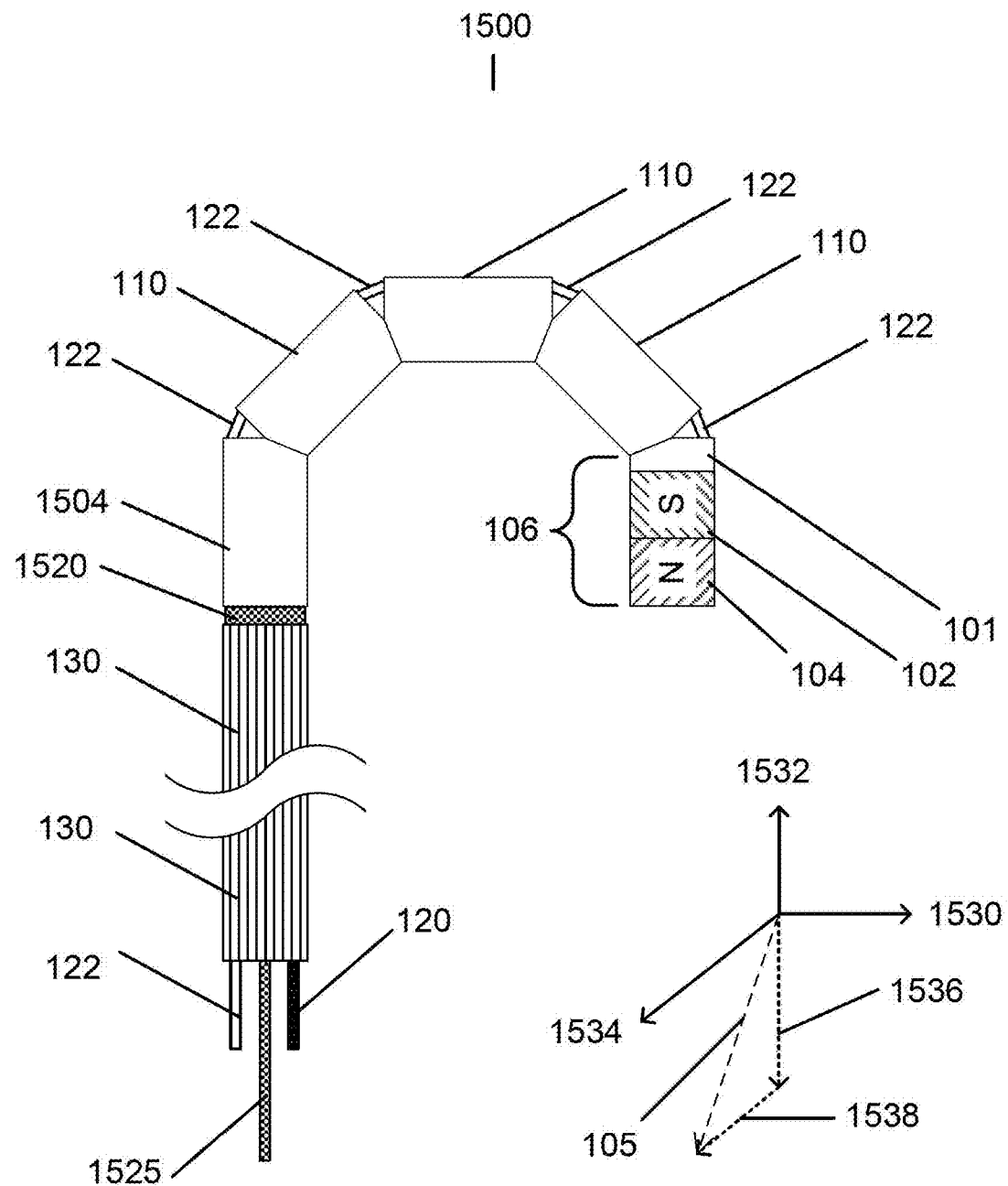
FIG. 15 is a drawing of another example of the magnetically-controlled linkage-based device according to one embodiment of the present invention possessing five linkages and four joints and a magnetic pivotable base.

FIG. 15 is a drawing of another example of the magnetically-controlled linkage-based device possessing five linkages and four joints and a magnetic pivotable base. A pivot 1520 is depicted which allows the five linkage elements (i.e., the linkage base 1504 plus three linkage body elements 110 plus the magnet tip subassembly 106) to turn about the support body 130. By applying an external magnetic field 105 which possesses a component 1538 out of the plane defined by the axes depicted by 1530 and 1532 so that the magnetic field component 1536 is in the plane identified by the axes labeled by 1532 and 1534, a magnetic torque will be generated which causes the magnetically-controlled linkage-based device to rotate on the pivot 1520 about the support body 130. The component of the external magnetic field 105 in the plane defined by axes depicted by 1530 and 1532 (identified by 1536 in the depiction 1500) controls the magnetically-controlled linkage-based device's deflection, which is shown as in a clockwise-like configuration. It may be beneficial in some cases to magnetize one or more of the linkage elements (i.e., linkage body elements 110 and/or the linkage base 1504) to generate additional torque of the linkage elements (110, 1504, 106) about the support body 130 via the pivot 1520. To apply friction or to hold the orientation, a pivot control wire 1525 is depicted which holds, locks, or tensions the orientation of the linkage base 1504 with respect to the support body 130 and the pivot 1520.

Figure 16:
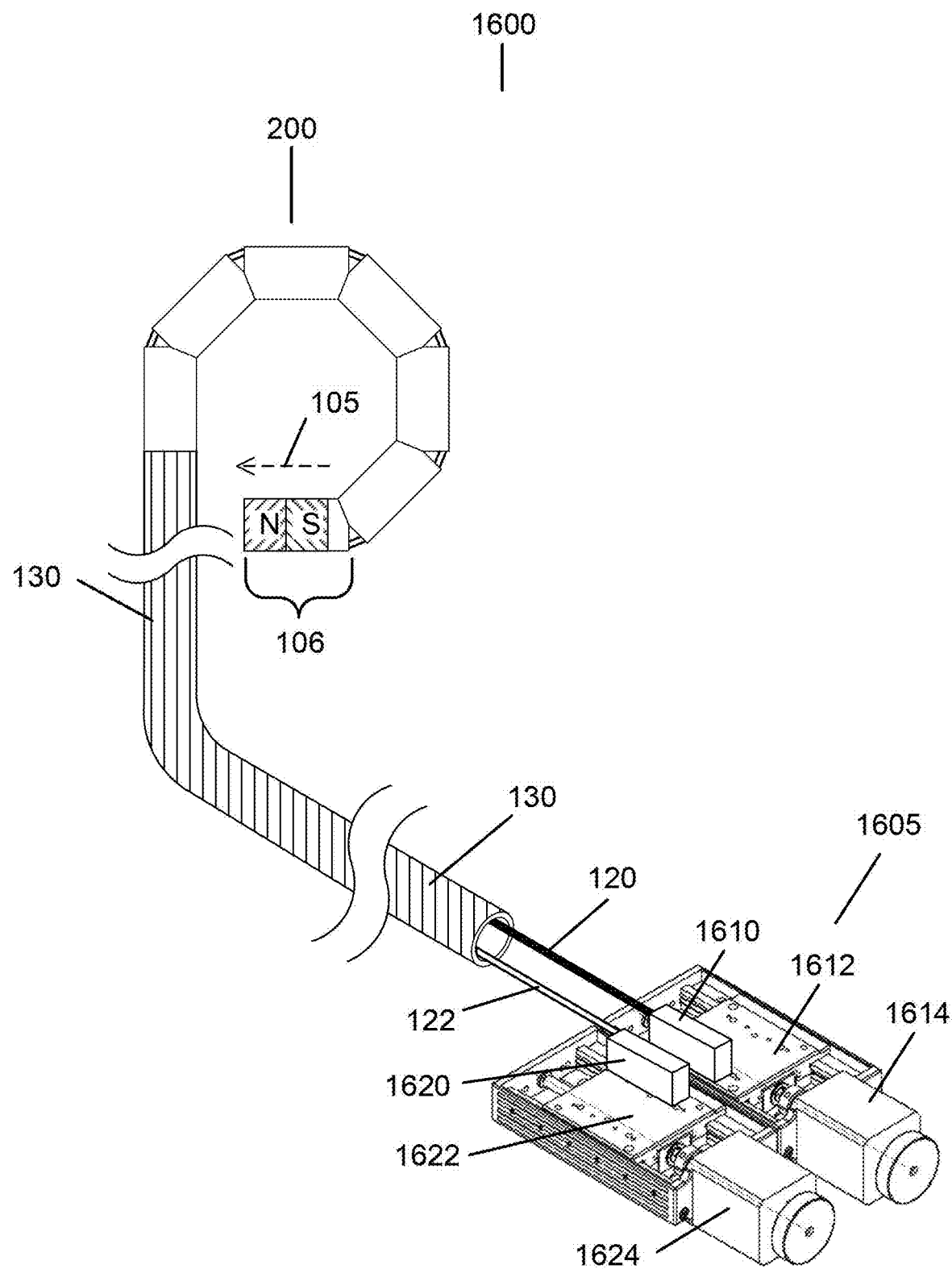
FIG. 16 is a drawing of an example wire controller for manipulating a magnetically-controlled linkage-based device.

FIG. 16 is a depiction 1600 of an example wire controller for manipulating a magnetically-controlled linkage-based device. For this example, two motors (1614 and 1624) are used to advance or retract the two control wires (120 and 122) which pass along the support body 130 and assist the external magnetic field 105 in controlling the configuration of the magnetically-controlled linkage-based device 200. In the depicted example, the inner control wire 120 is attached to a mounting block 1610, which is attached to a linear stage 1612. A motor 1614 controls the advancement or retraction of the inner control wire 120. Likewise, the outer control wire 122 is attached to a mounting block 1620, which is attached to a linear stage 1622. A motor 1624 controls the advancement or retraction of the outer control wire 120. In this arrangement, the movement of one control wire (e.g., 120) can be oppositely matched to the other control wire (e.g., 122). Also, both control wires (120 and 122) can be retracted to create tension, thereby holding a preferential configuration of the magnetically-controlled linkage-based device 200. Likewise, both control wires (120 and 122) can be relaxed to allow free motion of the magnetically-controlled linkage-based device linkages 200. Because forces applied to the magnet tip subassembly 106 result in forces being applied to the control wires (120 and 122), the control motor assembly 1605 can make use of load cells in the mounting blocks (1610 and 1620) to detect the forces applied to the magnetically-controlled linkage-based device's 200 magnet tip subassembly 106.

Figure 17:
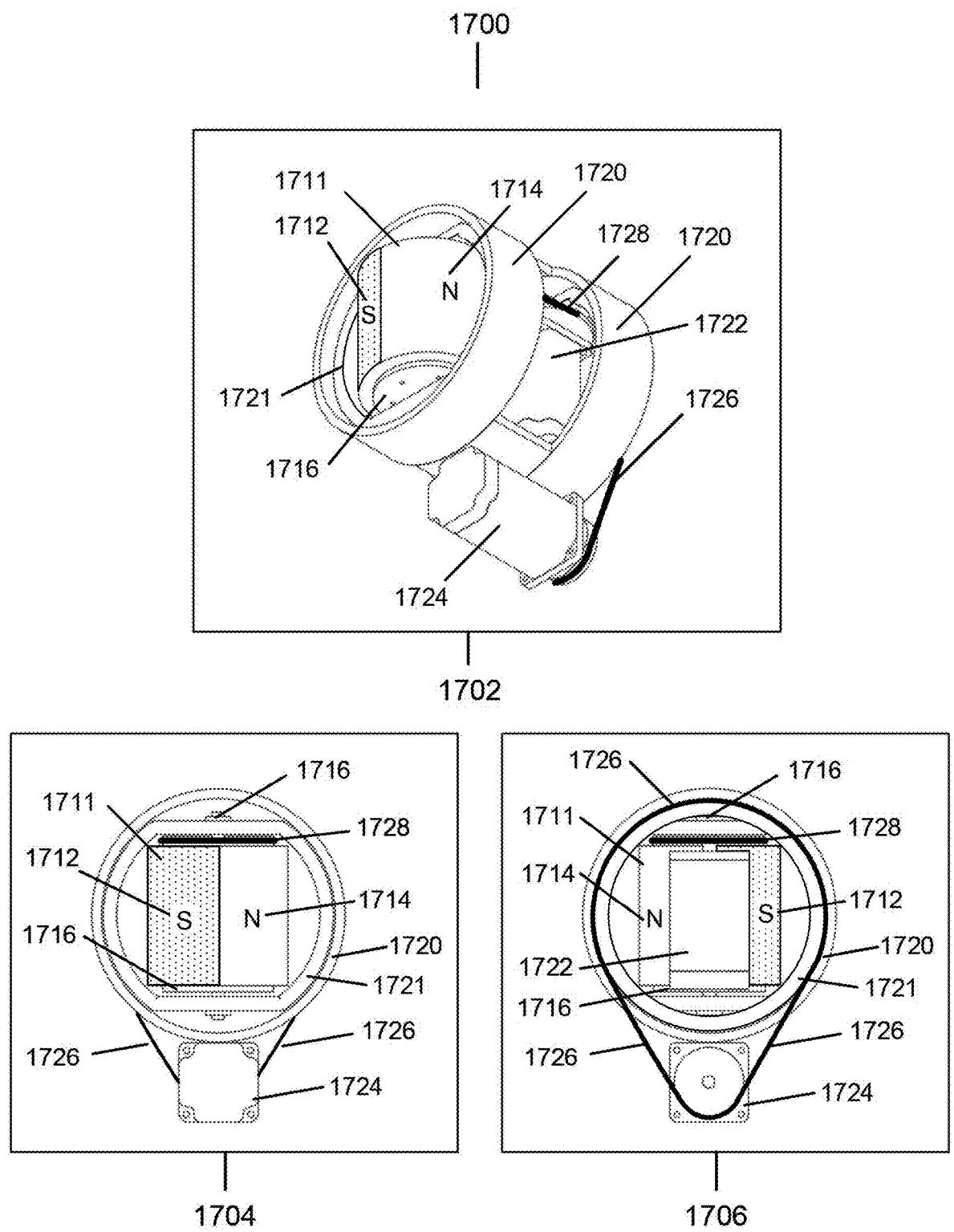
FIG. 17 is a drawing of an example external magnet system for generating a magnetic field and gradient to control the magnetically-controlled linkage-based device.

FIG. 17 is a drawing of an example external magnet system for generating a magnetic field and gradient to control the magnetically-controlled linkage-based device. Subfigure 1702 depicts the isometric view of the example external magnet system. Subfigure 1704 depicts the front view of the example external magnet system. Subfigure 1706 depicts the rear view of the example external magnet system. The permanent magnet subassembly 1711 possesses a North and South magnetic pole (1714 and 1712, respectively). The sides of the permanent magnet subassembly 1711 are connected to endplates 1716 which are free to spin within the inner yoke assembly 1721 so that the permanent magnet subassembly 1711 can rotate in a manner that the North 1714 and South 1712 magnet poles switch positions. To accomplish this, the magnet drive motor 1722 with the magnet drive belt 1728 attached to one of the endplates 1716 is used. The inner yoke assembly 1721 is allowed to rotate within the outer support frame 1720. To accomplish this, the inner yoke drive motor 1724 with the inner yoke drive belt 1726 attached to the inner yoke assembly 1721 is used. In this configuration, the inner yoke drive motor 1724 turns the inner yoke drive belt 1726 which imparts rotation on the inner yoke assembly 1721. The magnet drive motor 1722 turns the magnet drive belt 1728 so as to spin the permanent magnet subassembly 1711. As a result, the permanent magnet subassembly 1711 can achieve any orientation in space, thereby creating the preferred external magnetic field orientations and corresponding temporal behavior While the invention has been shown in several particular embodiments it should be clear that various modifications may be made to the present invention without departing from the spirit and scope thereof. The scope of the present invention is defined by the appended claims and equivalents thereto.

What is claimed is:

1. A magnetically controllable linkage based medical device for interventional medical procedures, the device comprising:
    a magnetic tip subassembly including magnet elements thereon located at a distal end of the medical device;
    a plurality of linkage body elements connected in sequence, a distal linkage body element coupled to the magnetic tip subassembly, wherein each linkage body element is configured for deflection in at least one deflection direction;
    a linkage base element coupled to a proximal linkage body element;
    a support body connected to the linkage base element;
    at least one pair of control wires passing within the support body, the linkage base element, and the linkage body elements to the magnetic tip subassembly; and
    wherein the device is configured such that an externally-generated magnetic field deflects the magnetic tip subassembly to at least one deflection angle, and wherein selectively tensioning the control wires holds the plurality of linkage body elements and linkage base element in a desired orientation,
    wherein the at least one deflection angle and the desired orientation are not constrained to a one-to-one relationship,
    wherein the magnetically controllable linkage based medical device does not experience a restoring force when the magnetic tip subassembly is deflected, and
    wherein the externally-generated magnetic field is operable to encode space to control the at least one deflection angle and the desired orientation of the plurality of linkage body elements.

2. The magnetically controllable linkage based medical device for interventional medical procedures according to claim 1, wherein retracting one control wire acts to straighten the magnetically-controlled linkage-based device and wherein the device is configured such that an externally-generated magnetic field of less than 25 millitesla deflects the magnetically-controlled linkage-based device by greater than or equal to 90 degrees in at least one deflection direction.

3. The magnetically controllable linkage based medical device for interventional medical procedures according to claim 1, wherein retracting one control wire acts to deflect the magnetically-controlled linkage-based device.

4. The magnetically controllable linkage based medical device for interventional medical procedures according to claim 1, wherein the plurality of linkage body elements defines a plane of rotation for the device.

5. The magnetically controllable linkage based medical device for interventional medical procedures according to claim 1, wherein at least one of the control wires is configured to break under specific force loads to minimize forces exerted on body tissue.

6. The magnetically controllable linkage based medical device for interventional medical procedures according to claim 1, wherein at least one of the control wires is operable to detect a force applied to the magnetic tip subassembly.

7. The magnetically controllable linkage based medical device for interventional medical procedures according to claim 1, wherein a fully-deflected configuration is configured to position the magnetic tip subassembly 270-degrees from a vertical non-deflected position.

8. The magnetically controllable linkage based medical device for interventional medical procedures according to claim 1, wherein one or more controllers is used to advance or retract the at least one pair of control wires.

9. The magnetically controllable linkage based medical device for interventional medical procedures according to claim 1, wherein the device is configured for delivery of ablative therapy for the treatment of atrial fibrillation.

10. The magnetically controllable linkage based medical device for interventional medical procedures according to claim 1, wherein the externally-generated magnetic field is operable to deflect the magnetic tip subassembly by greater than or equal to 45 degrees at less than 40 millitesla.

11. The magnetically controllable linkage based medical device for interventional medical procedures according to claim 1, wherein the magnetically controllable linkage based medical device does not experience a restoring force when the at least one deflection angle is greater than or equal to 90 degrees.

12. The magnetically controllable linkage based medical device for interventional medical procedures according to claim 1, wherein the pair of control wires comprise a nonelastic polymer material.

13. The magnetically controllable linkage based medical device for interventional medical procedures according to claim 1, wherein each of the linkage body elements are not constrained to a one-to-one relationship between one another.

14. The magnetically controllable linkage based medical device for interventional medical procedures according to claim 1, the magnetically controllable linkage based medical device further comprising one or more joints between each of the plurality of linkage body elements, wherein the externally-generated magnetic field is configured to articulate each joint of the one or more joints within and including a full range of angulation.

15. The magnetically controllable linkage based medical device for interventional medical procedures according to claim 1, wherein the desired orientation of the linkage body elements is operable to be controlled entirely by the externally-generated magnetic field and a motion of the magnetic tip subassembly.

16. The magnetically controllable linkage based medical device for interventional medical procedures according to claim 1, wherein the at least one pair of control wires are only operable to hold the desired orientation and are not operable to determine the desired orientation.

17. The magnetically controllable linkage based medical device for interventional medical procedures according to claim 1, the magnetically controllable linkage based medical device further comprising a collapsible film operable to prevent bodily fluids from entering the magnetically controllable linkage based device.

18. The magnetically controllable linkage based medical device for interventional medical procedures according to claim 1, wherein the externally-generated magnetic field is operable to encode space such that a single deflection angle of the magnetic tip subassembly results in two or more possible desired orientations of the linkage body elements.

19. A magnetically controllable linkage based medical device for interventional medical procedures, the device comprising:
    a magnetic tip subassembly including magnet elements thereon located at a distal end of the medical device;
    a plurality of linkage body elements connected in sequence, a distal linkage body element coupled to the magnetic tip subassembly, wherein each linkage body element is configured for deflection in at least one deflection direction;
a linkage base element coupled to a proximal linkage body element;
a support body connected to the linkage base element;
at least one pair of control wires passing within the support body, the linkage base element, and the linkage body elements to the magnetic tip subassembly; and
wherein the device is configured such that an externally-generated magnetic field deflects the magnetic tip subassembly to at least one deflection angle, and wherein selectively tensioning the control wires holds the plurality of linkage body elements and linkage base element in a desired orientation,
wherein the at least one deflection angle and the desired orientation are not constrained to a one-to-one relationship,
wherein the magnetically controllable linkage based medical device does not experience a restoring force when the magnetic tip subassembly is deflected,
wherein the externally-generated magnetic field is operable to encode space to control the at least one deflection angle and the desired orientation of the plurality of linkage body elements, and
wherein the externally-generated magnetic field is operable to encode space such that a single deflection angle of the magnetic tip subassembly results in two or more possible desired orientations of the plurality of linkage body elements.

20. A magnetically controllable linkage based medical device for interventional medical procedures, the device comprising:
a magnetic tip subassembly including magnet elements thereon located at a distal end of the medical device;
a plurality of linkage body elements connected in sequence, a distal linkage body element coupled to the magnetic tip subassembly, wherein each linkage body element is configured for deflection in at least one deflection direction;
one or more joints between each of the plurality of linkage body elements;
a linkage base element coupled to a proximal linkage body element;
a support body connected to the linkage base element;
at least one pair of control wires passing within the support body, the linkage base element, and the linkage body elements to the magnetic tip subassembly; and
wherein the device is configured such that an externally-generated magnetic field deflects the magnetic tip subassembly to at least one deflection angle, and wherein selectively tensioning the control wires holds the plurality of linkage body elements and linkage base element in a desired orientation,
wherein the at least one deflection angle and the desired orientation are not constrained to a one-to-one relationship,
wherein the magnetically controllable linkage based medical device does not experience a restoring force when the magnetic tip subassembly is deflected,
wherein the externally-generated magnetic field is operable to encode space to control the at least one deflection angle and the desired orientation of the plurality of linkage body elements, and
wherein the externally-generated magnetic field is configured to articulate each joint of the one or more joints within and including a full range of angulation to form the desired orientation.

* * * * *